(12) United States Patent
Frushell et al.

(10) Patent No.: US 9,028,556 B2
(45) Date of Patent: *May 12, 2015

(54) METHOD AND APPARATUS FOR RE-ATTACHING THE LABRUM OF A HIP JOINT

(71) Applicant: Pivot Medical, Inc., Sunnyvale, CA (US)

(72) Inventors: Matthew Frushell, Danville, CA (US); Julian Nikolchev, Portola Valley, CA (US); John Savarese, San Mateo, CA (US)

(73) Assignee: Pivot Medical, Inc., Sunnyvale, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 13/891,621

(22) Filed: May 10, 2013

(65) Prior Publication Data

US 2014/0088705 A1 Mar. 27, 2014

Related U.S. Application Data

(63) Continuation of application No. 12/148,676, filed on Apr. 21, 2008, now Pat. No. 8,454,704.

(60) Provisional application No. 60/925,478, filed on Apr. 20, 2007, provisional application No. 60/925,504, filed on Apr. 20, 2007, provisional application No. 61/068,290, filed on Mar. 6, 2008.

(51) Int. Cl.
*A61F 2/32* (2006.01)
*A61B 17/04* (2006.01)
*A61F 2/08* (2006.01)
*A61F 2/34* (2006.01)
*A61B 17/17* (2006.01)
*A61B 17/56* (2006.01)

(52) U.S. Cl.
CPC ......... *A61B 17/0401* (2013.01); *A61B 17/0469* (2013.01); *A61B 17/1796* (2013.01); *A61B 2017/0409* (2013.01); *A61B 2017/0412* (2013.01); *A61B 2017/564* (2013.01); *A61B 17/1746* (2013.01); *A61F 2/0811* (2013.01); *A61F 2/34* (2013.01)

(58) Field of Classification Search
CPC ................ A61F 2/32; A61F 2/34; A61F 2/36
USPC ............................... 623/22.11–23.4
See application file for complete search history.

(56) References Cited

U.S. PATENT DOCUMENTS

| | | | |
|---|---|---|---|
| 5,472,452 A | 12/1995 | Trott | |
| 5,584,835 A | 12/1996 | Greenfield | |
| 5,632,761 A | 5/1997 | Smith et al. | |
| 5,683,419 A | 11/1997 | Thal | |
| 5,700,266 A | 12/1997 | Harryman, II | |

(Continued)

OTHER PUBLICATIONS

Crawford, J.R. et al., Current Concepts in the Management of Femoroacetabular Impingement, The Journal of Bone & Joint Surgery, Nov. 2005, pp. 1459-1462, vol. 87B, No. 11.

(Continued)

*Primary Examiner* — Jason-Dennis Stewart
(74) *Attorney, Agent, or Firm* — Pandiscio & Pandiscio

(57) ABSTRACT

A method and apparatus for re-attaching the labrum of a hip joint.

15 Claims, 39 Drawing Sheets

(56) References Cited

U.S. PATENT DOCUMENTS

| | | |
|---|---|---|
| 5,728,136 A | 3/1998 | Thal |
| 5,782,864 A | 7/1998 | Lizardi |
| 5,957,953 A | 9/1999 | Dipoto et al. |
| 6,050,998 A | 4/2000 | Fletcher |
| RE37,963 E | 1/2003 | Thal |
| 2002/0095214 A1 | 7/2002 | Hyde, Jr. |
| 2003/0195563 A1 | 10/2003 | Foerster |
| 2004/0098052 A1 | 5/2004 | West et al. |
| 2004/0138683 A1 | 7/2004 | Shelton et al. |
| 2005/0245932 A1 | 11/2005 | Fanton et al. |
| 2005/0283102 A1 | 12/2005 | Schwenn et al. |
| 2006/0079904 A1 | 4/2006 | Thal |
| 2006/0106423 A1 | 5/2006 | Weisel et al. |
| 2007/0049931 A1 | 3/2007 | Justis et al. |
| 2007/0142838 A1 | 6/2007 | Jordon |
| 2007/0156153 A1 | 7/2007 | Jiang et al. |
| 2007/0156176 A1 | 7/2007 | Fanton et al. |
| 2008/0051836 A1 | 2/2008 | Foerster et al. |
| 2008/0255613 A1 | 10/2008 | Kaiser et al. |
| 2009/0069823 A1 | 3/2009 | Foerster et al. |
| 2009/0138042 A1 | 5/2009 | Thal |

OTHER PUBLICATIONS

Kelly, Brian T. et al., Arthroscopic Labral Repair in the Hip: Surgical Technique and Review of the Literature, Arthmisoopy: The Journal of Arthroscopic and Related Surgery, Dec. 2005, pp. 1496-1504. volume 21, No. 12.

Philippon et al., A New Method for Acetabular Rim Trimming and Labral Repair, Clinics in Sports Medicine, Apr. 2006, vol. 25, pp. 293-297.

CAM-TYPE FEMOROACETABULAR IMPINGEMENT (FAI)
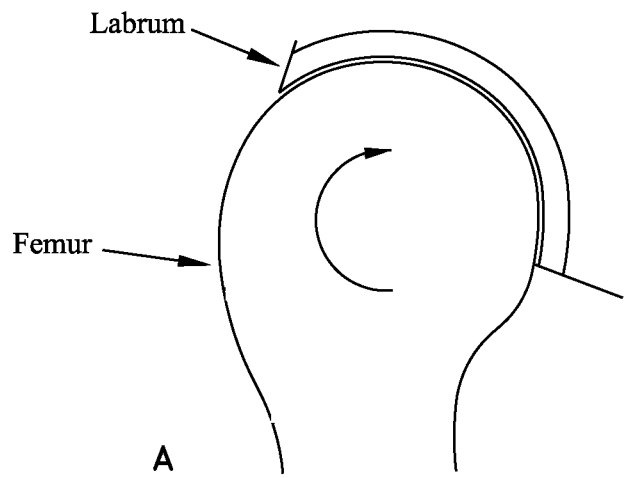
CAM INJURY TO THE LABRUM
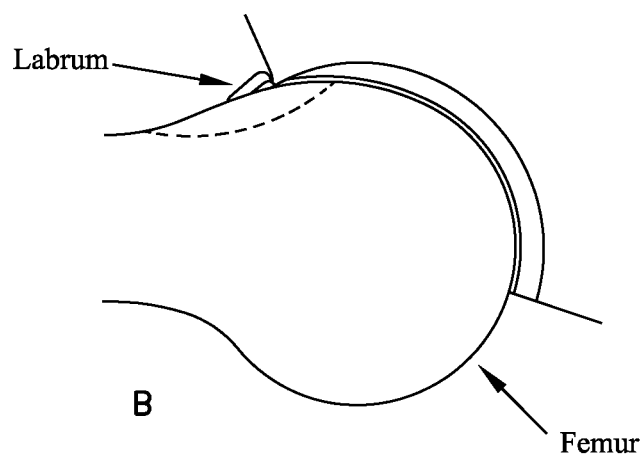
FIG. 13

PINCER-TYPE FEMOROACETABULAR IMPINGEMENT (FAI)
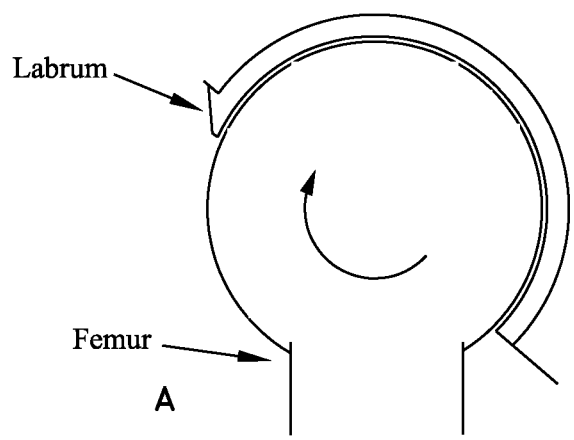
PINCER INJURY TO THE LABRUM
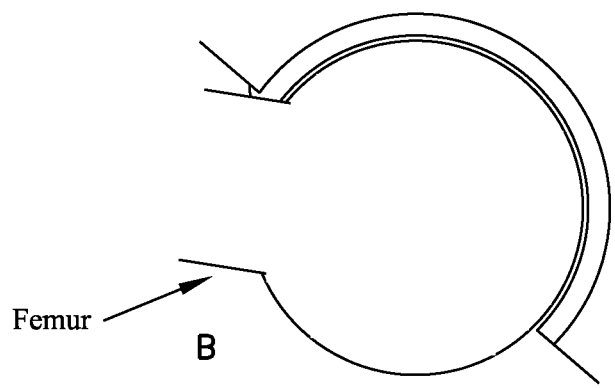
FIG. 14

METHOD AND APPARATUS FOR RE-ATTACHING THE LABRUM OF A HIP JOINT

REFERENCE TO PENDING PRIOR PATENT APPLICATIONS

This patent application is a continuation of pending prior U.S. patent application Ser. No. 12/148,676, filed Apr. 21, 2008 by Matthew Frushell at al. for METHOD AND APPARATUS FOR RE-ATTACHING THE LABRUM OF A HIP JOINT, which in turn claims benefit of:

(i) prior U.S. Provisional Patent Application Ser. No. 60/925,478, filed Apr. 20, 2007 by Julian Nikolchev for METHOD AND APPARATUS FOR RECONSTRUCTING THE HIP JOINT;

(ii) prior U.S. Provisional Patent Application Ser. No. 60/925,504, filed Apr. 20, 2007 by Julian Nikolchev at al. for METHOD AND APPARATUS FOR RECONSTRUCTING THE HIP JOINT; and (iii) prior U.S. Provisional Patent Application Ser. No. 61/068,290, filed Mar. 6, 2008 by Matthew Frushell for METHOD AND APPARATUS FOR RE-ATTACHING THE LABRUM OF A HIP JOINT.

The above-identified patent applications are hereby incorporated herein by reference.

FIELD OF THE INVENTION

This invention relates to surgical methods and apparatus in general, and more particularly to methods and apparatus for treating the hip joint.

BACKGROUND OF THE INVENTION

The Hip Joint in General

The hip joint is a ball-and-socket joint which movably connects the leg to the torso. The hip joint is capable of a wide range of different motions, e.g., flexion and extension, abduction and adduction, medial and lateral rotation, etc. See FIGS. 1A, 1B, 1C and 1D. With the possible exception of the shoulder joint, the hip joint is perhaps the most mobile joint in the body. Significantly, and unlike the shoulder joint, the hip joint carries substantial weight loads during most of the day, in both static (e.g., standing and sitting) and dynamic (e.g., walking and running) conditions.

The hip joint is susceptible to a number of different pathologies. These pathologies can have both congenital and injury-related origins. In some cases, the pathology can be substantial at the outset. In other cases, the pathology may be minor at the outset but, if left untreated, may worsen over time. More particularly, in many cases, an existing pathology may be exacerbated by the dynamic nature of the hip joint and the substantial weight loads imposed on the hip joint.

The pathology may, either initially or thereafter, significantly interfere with patient comfort and lifestyle. In some cases, the pathology can be so severe as to require partial or total hip replacement. A number of procedures have been developed for treating hip pathologies short of partial or total hip replacement, but these procedures are generally limited in scope due to the significant difficulties associated with treating the hip joint.

A better understanding of various hip joint pathologies, and also the current limitations associated with their treatment, can be gained from a more thorough understanding of the anatomy of the hip joint.

Anatomy of the Hip Joint

The hip joint is formed at the junction of the femur and the hip. More particularly, and looking now at FIG. 2, the ball of the femur is received in the acetabular cup of the hip, with a plurality of ligaments and other soft tissue serving to hold the bones in articulating condition.

More particularly, and looking now at FIG. 3, the femur is generally characterized by an elongated body terminating, at its top end, in an angled neck which supports a hemispherical head (also sometimes referred to as "the ball"). As seen in FIGS. 3 and 4, a large projection known as the greater trochanter protrudes laterally and posteriorly from the elongated body adjacent to the neck of the femur. A second, somewhat smaller projection known as the lesser trochanter protrudes medially and posteriorly from the elongated body adjacent to the neck. An intertrochanteric crest (FIGS. 3 and 4) extends along the periphery of the femur, between the greater trochanter and the lesser trochanter.

Looking next at FIG. 5, the hip socket is made up of three constituent bones: the ilium, the ischium and the pubis. These three bones cooperate with one another (they typically ossify into a single "hip bone" structure around the age of 25 or so) so as to collectively form the acetabular cup. The acetabular cup receives the head of the femur.

Both the head of the femur and the acetabular cup are covered with a layer of articular cartilage which protects the underlying bone and facilitates motion. See FIG. 6.

Various ligaments and soft tissue serve to hold the ball of the femur in place within the acetabular cup. More particularly, and looking now at FIGS. 7 and 8, the ligamentum teres extends between the ball of the femur and the base of the acetabular cup. As seen in FIG. 9, a labrum is disposed about the perimeter of the acetabular cup. The labrum serves to increase the depth of the acetabular cup and effectively establishes a suction seal between the ball of the femur and the rim of the acetabular cup, thereby helping to hold the head of the femur in the acetabular cup. In addition to the foregoing, and looking now at FIG. 10, a fibrous capsule extends between the neck of the femur and the rim of the acetabular cup, effectively sealing off the ball-and-socket members of the hip joint from the remainder of the body. The foregoing structures (i.e., the ligamentum teres, the labrum and the fibrous capsule) are encompassed and reinforced by a set of three main ligaments (i.e., the iliofemoral ligament, the ischiofemoral ligament and the pubofemoral ligament) which extend between the femur and the perimeter of the hip socket. See FIGS. 11 and 12.

Pathologies of the Hip Joint

As noted above, the hip joint is susceptible to a number of different pathologies. These pathologies can have both congenital and injury-related origins.

By way of example but not limitation, one important type of congenital pathology of the hip joint involves impingement between the neck of the femur and the rim of the acetabular cup. In some cases, and looking now at FIG. 13, this impingement can occur due to irregularities in the geometry of the femur. This type of impingement is sometimes referred to as a cam-type femoroacetabular impingement (i.e., a cam-type FAI). In other cases, and looking now at FIG. 14, the impingement can occur due to irregularities in the geometry of the acetabular cup. This latter type of impingement is sometimes referred to as a pincer-type femoroacetabular impingement (i.e., a pincer-type FAI). Impingement can result in a reduced range of motion, substantial pain and, in some cases, significant deterioration of the hip joint.

By way of further example but not limitation, another important type of congenital pathology of the hip joint involves defects in the articular surface of the ball and/or the articular surface of the acetabular cup. Defects of this type sometimes start fairly small but often increase in size over time, generally due to the dynamic nature of the hip joint and also due to the weight-bearing nature of the hip joint. Articular defects can result in substantial pain, induce and/or exacerbate arthritic conditions and, in some cases, cause significant deterioration of the hip joint.

By way of further example but not limitation, one important type of injury-related pathology of the hip joint involves trauma to the labrum. More particularly, in many cases, an accident or sports-related injury can result in the labrum being torn away from the rim of the acetabular cup, typically with a tear running through the body of the labrum. See FIG. 15. These types of injuries can be very painful for the patient and, if left untreated, can lead to substantial deterioration of the hip joint.

The General Trend Toward Treating Joint Pathologies Using Minimally-Invasive, and Earlier, Interventions The current trend in orthopedic surgery is to treat joint pathologies using minimally-invasive techniques. Such minimally-invasive, "keyhole" surgeries generally offer numerous advantages over traditional, "open" surgeries, including reduced trauma to the patient's tissue, less pain for the patient, faster recuperation times, etc.

By way of example but not limitation, it is common to re-attach ligaments in the shoulder joint using minimally-invasive, "keyhole" techniques which do not require laying open the capsule of the shoulder joint. By way of further example but not limitation, it is common to repair torn meniscal cartilage in the knee joint, and/or to replace ruptured ACL ligaments in the knee joint, using minimally-invasive techniques.

While such minimally-invasive approaches can require additional training on the part of the surgeon, such procedures generally offer substantial advantages for the patient and have now become the standard of care for many shoulder joint and knee joint pathologies.

In addition to the foregoing, in view of the inherent advantages and widespread availability of minimally-invasive approaches for treating pathologies of the shoulder joint and knee joint, the current trend is to provide such treatment much earlier in the lifecycle of the pathology, so as to address patient pain as soon as possible and so as to minimize any exacerbation of the pathology itself. This is in marked contrast to traditional surgical practices, which have generally dictated postponing surgical procedures as long as possible so as to spare the patient from the substantial trauma generally associated with invasive surgery.

Treatment for Pathologies of the Hip Joint

Unfortunately, minimally-invasive treatments for pathologies of the hip joint have lagged far behind minimally-invasive treatments for pathologies of the shoulder joint and knee joint. This is generally due to (i) the constrained geometry of the hip joint itself, and (ii) the nature and location of the pathologies which must typically be addressed in the hip joint.

More particularly, the hip joint is generally considered to be a "tight" joint, in the sense that there is relatively little room to maneuver within the confines of the joint itself. This is in marked contrast to the shoulder joint and the knee joint, which are generally considered to be relatively spacious when compared to the hip joint. As a result, it is relatively difficult for surgeons to perform minimally-invasive procedures on the hip joint.

Furthermore, the pathways for entering the interior of the hip joint (i.e., the pathways which exist between adjacent bones) are generally much more constraining for the hip joint than for the shoulder joint or the knee joint. This limited access further complicates effectively performing minimally-invasive procedures on the hip joint.

In addition to the foregoing, the nature and location of the pathologies of the hip joint also complicate performing minimally-invasive procedures on the hip joint. By way of example but not limitation, consider a typical detachment of the labrum in the hip joint. In this situation, instruments must generally be introduced into the joint space using an angle of approach which is set at approximately a right angle to the angle of re-attachment. This makes drilling into bone, for example, much more complex than where the angle of approach is effectively aligned with the angle of re-attachment, such as is frequently the case in the shoulder joint. Furthermore, the working space within the hip joint is typically extremely limited, further complicating repairs where the angle of approach is not aligned with the angle of re-attachment.

As a result of the foregoing, minimally-invasive hip joint procedures are still relatively difficult to perform and relatively uncommon in practice. Consequently, patients are typically forced to manage their hip pain for as long as possible, until a resurfacing procedure or a partial or total hip replacement procedure can no longer be avoided. These procedures are generally performed as a highly-invasive, open procedure, with all of the disadvantages associated with highly-invasive, open procedures.

As a result, there is a pressing need for improved methods and apparatus for reconstructing the hip joint.

Re-Attaching the Labrum of a Hip Joint

As noted above, hip arthroscopy is becoming increasingly more common in the diagnosis and treatment of various hip pathologies. However, due to the anatomy of the hip joint and the pathologies associated with the same, hip arthroscopy is currently practical for only selected pathologies and, even then, hip arthroscopy has generally met with limited success.

One procedure which is sometimes attempted arthroscopically relates to the repair of a torn and/or detached labrum. This procedure may be attempted (i) when the labrum has been damaged but is still sufficiently healthy and intact as to be capable of repair and/or re-attachment, and/or (ii) when the labrum has been deliberately detached (e.g., so as to allow for acetabular rim trimming in order to treat a pathology such as a pincer-type FAI) and needs to be subsequently re-attached. See, for example, FIG. 16, which shows a normal labrum attached to the acetabular cup, and FIG. 17, which shows the labrum detached from the acetabular cup. In this respect it should also be appreciated that repairing the labrum rather than removing the labrum is generally desirable, inasmuch as studies have shown that patients whose labrum has been repaired tend to have better long-term outcomes than patients whose labrum has been removed.

Unfortunately, current methods and apparatus for arthroscopically re-attaching the labrum are somewhat problematic. Thus, there is a need to improve upon the current approaches for labrum re-attachment.

More particularly, current approaches for arthroscopically re-attaching the labrum typically use conventional tissue re-attachment techniques. For example, one such technique requires that a screw-type bone anchor, with two sutures extending therefrom, be positioned in the acetabulum above the labrum re-attachment site, i.e., on the acetabulum shelf, opposing the capsule. Using known techniques for manipulating sutures arthroscopically, one of the sutures is passed either through the detached labrum or, alternatively, around the detached labrum. Then the first suture is tied to the second suture so as to draw the labrum toward the acetabulum shelf and hence against the acetabular rim. See FIG. 18.

Unfortunately, it can be difficult to pass suture through or around the labrum in order to re-attach the labrum to the acetabulum. This is due to space limitations within the hip joint, the angle of approach, etc.

This is particularly true when one considers the nature of the labrum and its anatomical position within the hip joint.

More particularly, the labrum is a relatively thin structure which normally sits on the inside surface of the acetabular cup (see FIG. 16). In some ways, the labrum has a geometry which is somewhat similar to a layer of an onion: it has a large surface area but a relatively thin depth. This thin depth presents a problem when passing a suture through the labrum.

Furthermore, the labrum is made up of a large number of filaments arranged in a generally concentric configuration. Thus, in order to prevent a passed suture from pulling back through the labrum, it is important to pass the suture through the labrum with a lateral offset between the entry and exit points so that the suture crosses a number of different labrum filaments. This can be difficult to do arthroscopically within the hip joint.

Furthermore, labral re-attachment utilizing a bone anchor set into the acetabular shelf creates a suture path, and hence a labral draw force, which is not directly aligned with the portion of the acetabular rim where the labrum is to be re-attached. As a result, an "indirect" draw force (also known as eversion) is applied to the labrum, i.e., the labrum is drawn around the rim of the acetabulum rather than directly into the acetabulum. This can sometimes result in a problematic labral re-attachment and, ultimately, can lead to a loss of the suction seal between the labrum and femoral head, which is a desired outcome of the procedure.

Accordingly, a primary object of the present invention is to provide a new approach for passing suture through the labrum so as to facilitate securing the labrum to the acetabulum in an anatomically-appropriate manner, thereby re-establishing the suction seal.

Another object of the present invention is to pass the suture through the labrum quickly and easily, and with a lateral offset, so that the suture crosses a number of different filaments.

A further object of the present invention is to apply a more direct labral draw force (i.e., one directly into the rim of the acetabulum) so as to provide a superior labral re-attachment and thereby re-establish the suction seal of the hip joint.

SUMMARY OF THE INVENTION

The present invention provides a novel method and apparatus for re-attaching the labrum to the acetabulum.

More particularly, the present invention provides a new approach for passing suture through the labrum so as to facilitate securing the labrum to the acetabulum in an anatomically-appropriate manner, thereby re-establishing the suction seal.

And the present invention provides a new approach for passing the suture through the labrum quickly and easily, and with a lateral offset, so that the suture crosses a number of different filaments.

Furthermore, the present invention applies a more direct labral draw force (i.e., one directly into the rim of the acetabulum) so as to provide a superior labral re-attachment and thereby re-establishes the suction seal of the hip joint.

In one preferred form of the present invention, there is provided apparatus for securing an object to bone, comprising:

a length of suture having a first end and a second end;

a first dart comprising a body and a distal tip configured for passing through the object and into the bone, the first end of the suture being secured to the first dart with a first connection; and a second dart comprising a body and a distal tip configured for passing through the object and into the bone, the second end of the suture being secured to the second dart with a second connection;

wherein at least one of the first connection and the second connection is adjustable so as to permit cinching of the suture after the first and second darts have been deployed in the bone.

In another form of the present invention, there is provided a method for securing an object to bone, comprising:

providing apparatus for securing an object to bone, wherein the apparatus comprises:

a length of suture having a first end and a second end;

a first dart comprising a body and a distal tip configured for passing through the object and into the bone, the first end of the suture being secured to the first dart with a first connection; and a second dart comprising a body and a distal tip configured for passing through the object and into the bone, the second end of the suture being secured to the second dart with a second connection;

wherein at least one of the first connection and the second connection is adjustable so as to permit cinching of the suture after the first and second darts have been deployed in the bone;

passing the first dart through the object at a first location and into the bone adjacent the first location;

passing the second dart through the object at a second location and into the bone adjacent the second location, wherein the second location is laterally and vertically displaced from the first location; and cinching the suture so as to make the suture taut against the object.

In another form of the present invention, there is provided an obturator for enlarging an opening in fibrous tissue, the obturator comprising:

a cannulated body having an atraumatic distal end characterized by a blunt distal tip followed by a pair of diametrically-opposed wings, whereby the blunt distal tip initially opens the fibers and the diametrically-opposed wings thereafter laterally widen the opening between the fibers.

In another form of the present invention, there is provided apparatus for securing an object to bone, comprising:

a length of suture having a first end and a second end;

a dart comprising a body and a distal tip configured for passing through the object and into the bone, the first end of the suture being fixedly secured to the dart with a first connection and the second end of the suture being securable to the dart with a second connection;

whereby the dart may be passed through the object and into the bone while the second end of the suture is detached from the dart, and the second end of the suture may thereafter be adjustably secured to the dart and cinched so as to secure the object against the bone.

In another form of the present invention, there is provided a method for securing an object to bone, comprising:

providing apparatus for securing an object to bone, wherein the apparatus comprises:

a length of suture having a first end and a second end;

a dart comprising a body and a distal tip configured for passing through the object and into the bone, the first end of the suture being fixedly secured to the dart with a first connection and the second end of the suture being securable to the dart with a second connection;

passing the dart through the object and into the bone; and adjustably securing the second end of the suture to the dart and cinching so as to make the suture taut against the object.

In another form of the present invention, there is provided apparatus for securing an object to bone, comprising:

a length of suture having a first end and a second end;

a dart comprising a body having a recess and a distal tip configured for passing through the object and into the bone, the first end of the suture being fixedly secured to the dart; and a compressible collet having a bore therethrough and being selectively receivable within the recess of the dart, wherein the collet is configured to slidably receive the suture therethrough when the collet is outside the recess of the dart, and further wherein the collet is configured to compress the bore and grip the suture when the collet is within the recess of the dart.

In another form of the present invention, there is provided a method for securing an object to bone, comprising:

providing apparatus for securing an object to bone, wherein the apparatus comprises:

a length of suture having a first end and a second end;

a dart comprising a body having a recess and a distal tip configured for passing through the object and into the bone, the first end of the suture being fixedly secured to the dart; and a compressible collet having a bore therethrough and being selectively receivable within the recess of the dart, wherein the collet is configured to slidably receive the suture therethrough when the collet is outside the recess of the dart, and further wherein the collet is configured to compress the bore and grip the suture when the collet is within the recess of the dart.

passing the dart through the object and into the bone; and passing the collet over the second end of the suture and down the length of the suture and into the recess so as to create a cinched loop of suture securing the object to the dart and hence to the bone.

In another form of the present invention, there is provided apparatus for securing an object to bone, comprising:

a length of suture having a first end and a second end;

at least three bone anchors attached to the suture, wherein the first end of the suture is fixedly secured to the first bone anchor, the second end of the suture is attached to the last bone anchor, and the intermediate portion of the suture being attached to the intermediate bone anchors.

In another form of the present invention, there is provided a method for securing an object to bone, comprising:

providing apparatus for securing an object to bone, wherein the apparatus comprises:

a length of suture having a first end and a second end;

at least three bone anchors attached to the suture, wherein the first end of the suture is fixedly secured to the first bone anchor, the second end of the suture is attached to the last bone anchor, and the intermediate portion of the suture being attached to the intermediate bone anchors;

passing the first bone anchor through the object at a first location and into the bone at a point laterally and vertically displaced from the first location;

successively passing each intermediate bone anchor through the object at a location which is laterally displaced from the immediately-preceding location and into the bone at a point laterally and vertically displaced from that location; and passing the last bone anchor through the object at a last location which is laterally displaced from the immediately-preceding location and into the bone at a point laterally and vertically displaced from the last location.

In another form of the present invention, there is provided a method for treating pincer-type femoroacetabular impingement (FAI), comprising:

detaching the labrum from the overgrown acetabular portion which is to be removed in order to alleviate the impingement;

removing the overgrown acetabular portion in order to alleviate the impingement, thereby providing a newly-trimmed acetabular rim surface; and securing the detached labrum to the newly-trimmed acetabular rim surface.

BRIEF DESCRIPTION OF THE DRAWINGS

These and other objects and features of the present invention will be more fully disclosed or rendered obvious by the following detailed description of the preferred embodiments of the invention, which is to be considered together with the accompanying drawings wherein like numbers refer to like parts, and further wherein:

FIG. 13 is a schematic view showing cam-type femoroacetabular impingement (FAI);

FIG. 14 is a schematic view showing pincer-type femoroacetabular impingement (FAI);

DETAILED DESCRIPTION OF THE INVENTION

The present invention provides a novel method and apparatus for re-attaching the labrum to the acetabulum.

The present invention also provides a novel method and apparatus for treating pincer-type FAI.

Figure 1A:
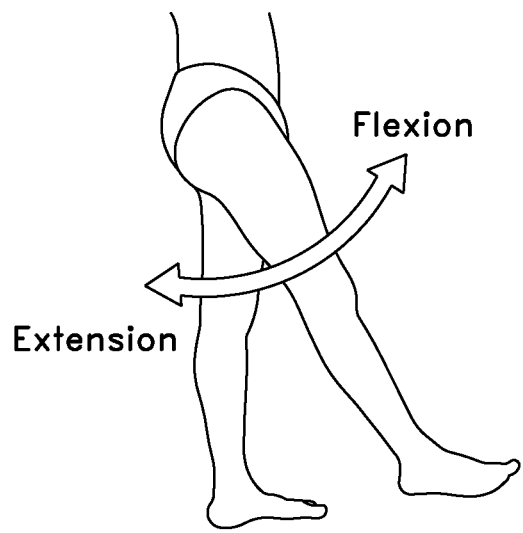
FIGS. 1A-1D are schematic views showing various aspects of hip motion.
Figure 1B:
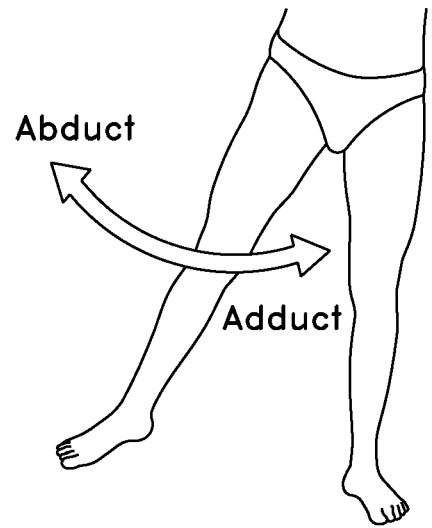
Figure 1C:
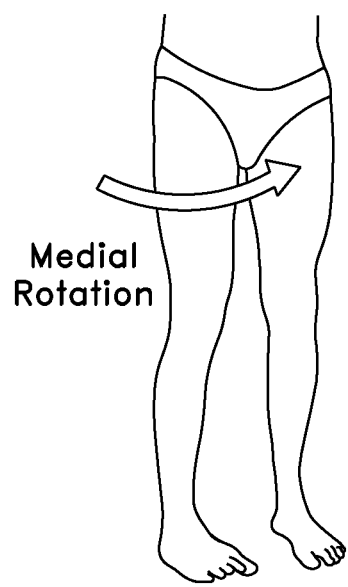
Figure 1D:
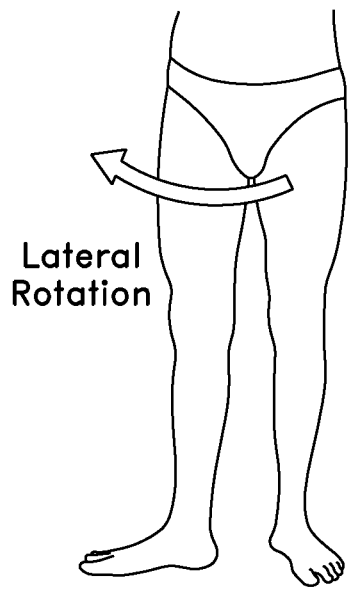
Figure 2:
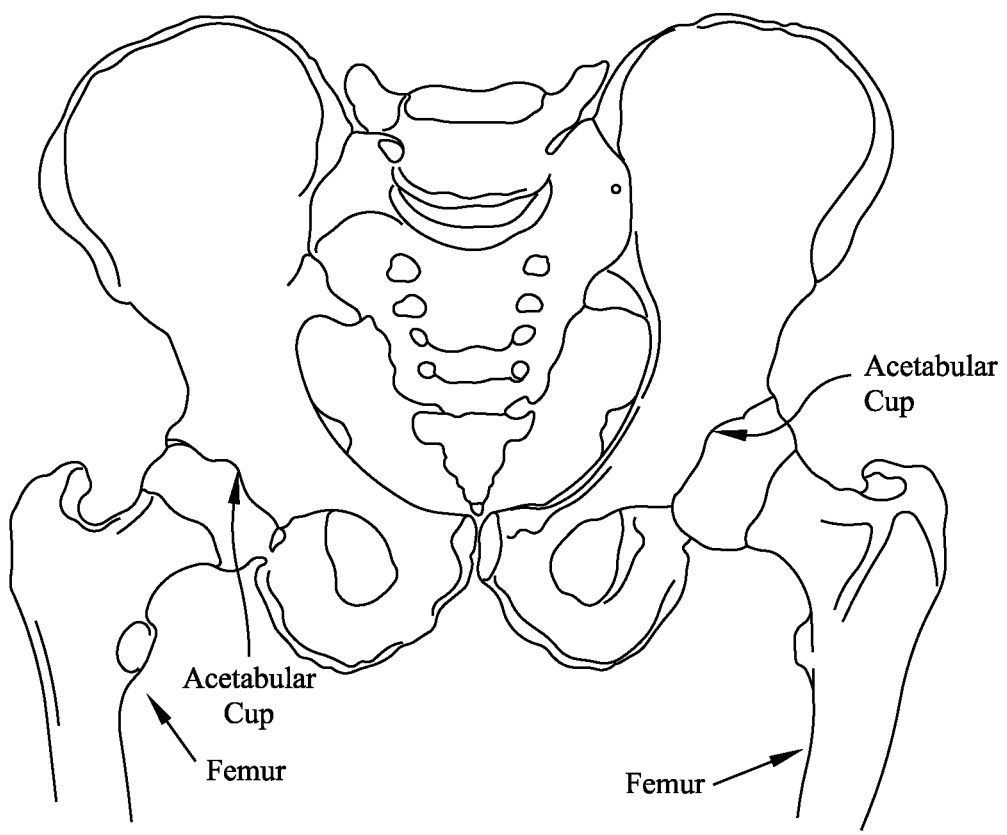
FIG. 2 is a schematic view showing the bone structure in the region of the hip joints.
Figure 3:
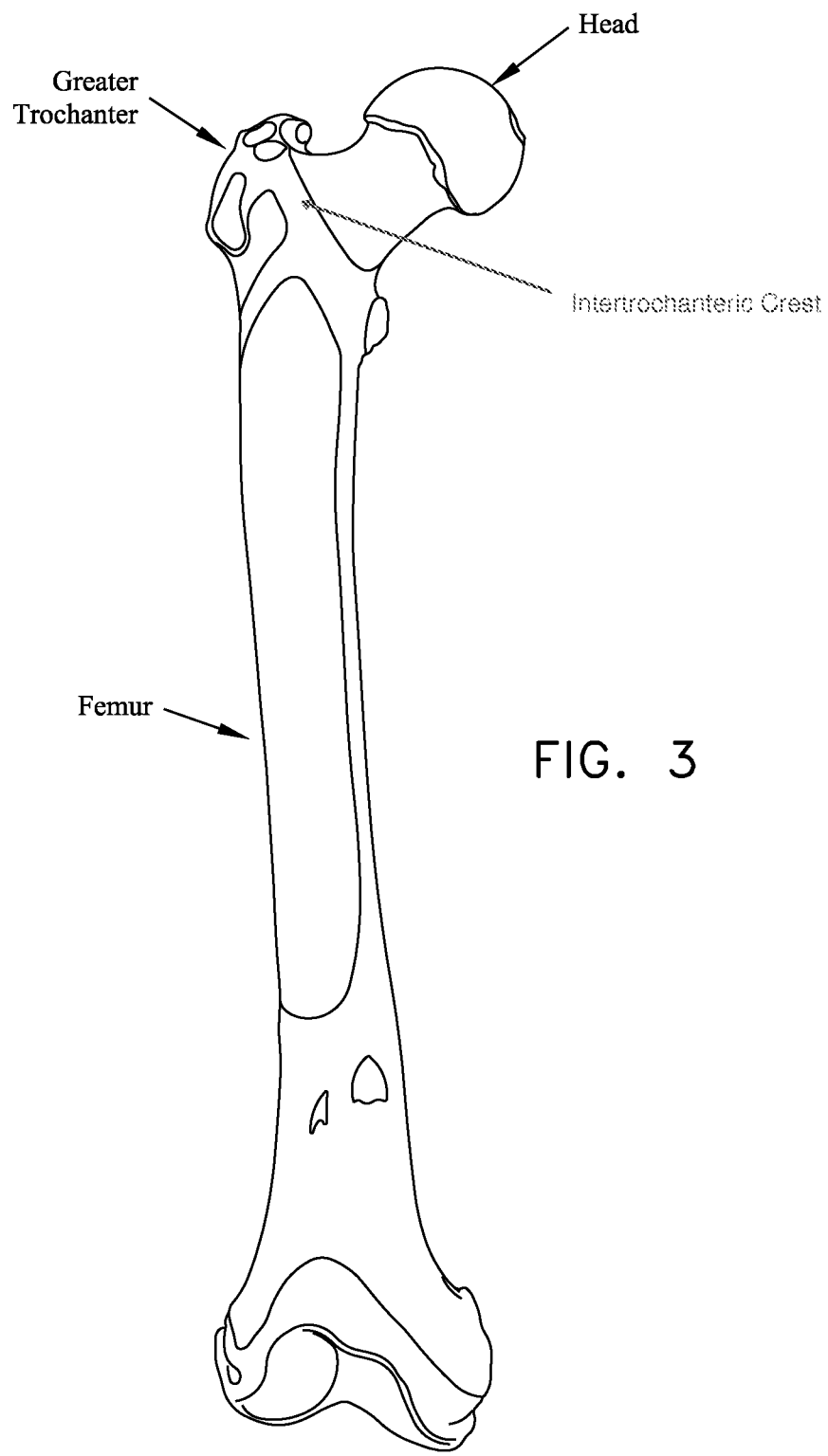
FIG. 3 is a schematic view of the femur.
Figure 4:
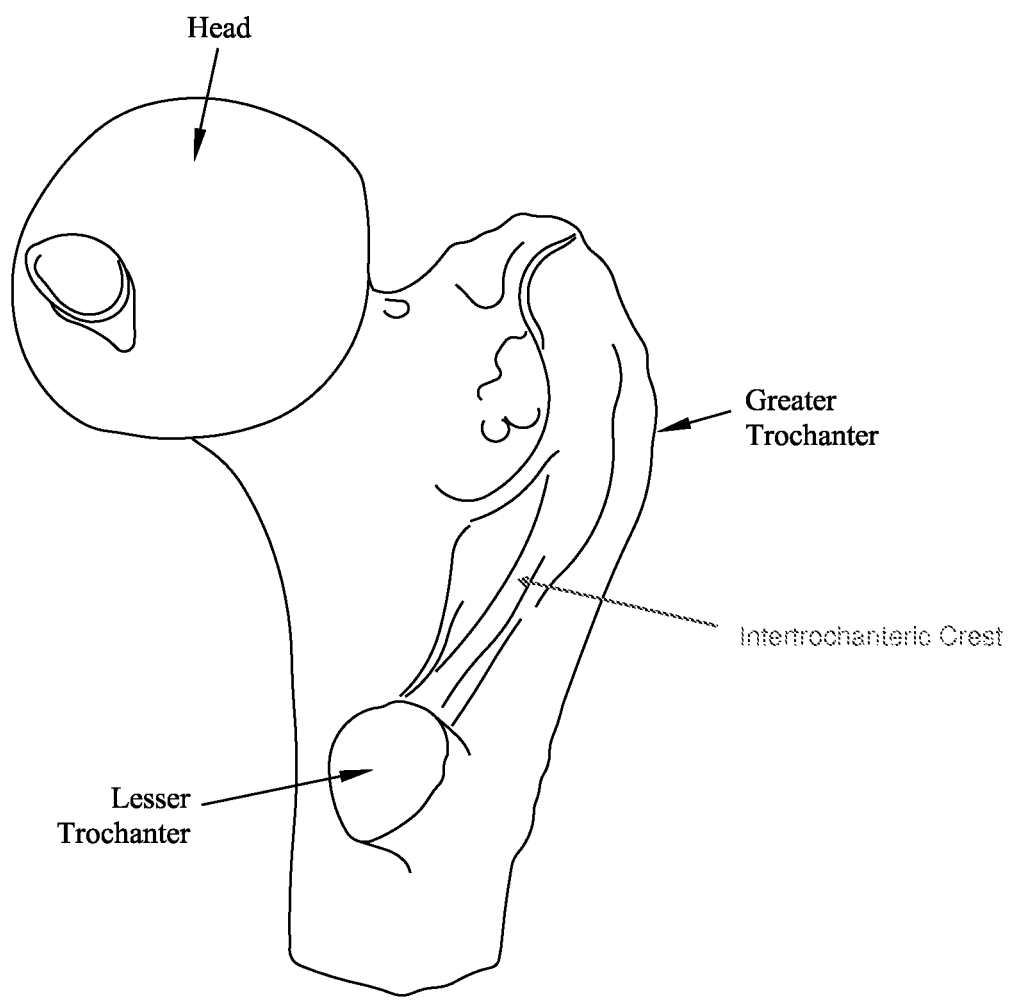
FIG. 4 is a schematic view of the top end of the femur.
Figure 5:
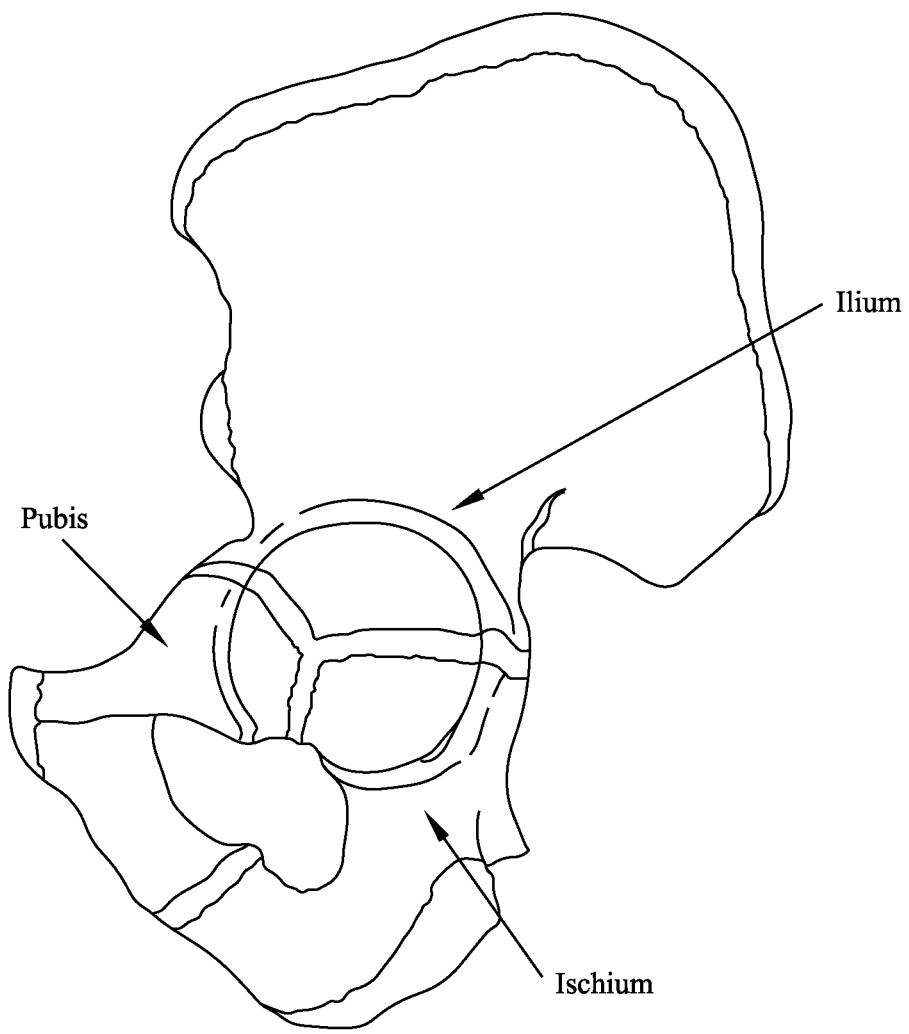
FIG. 5 is a schematic view of the pelvis.
Figure 6:
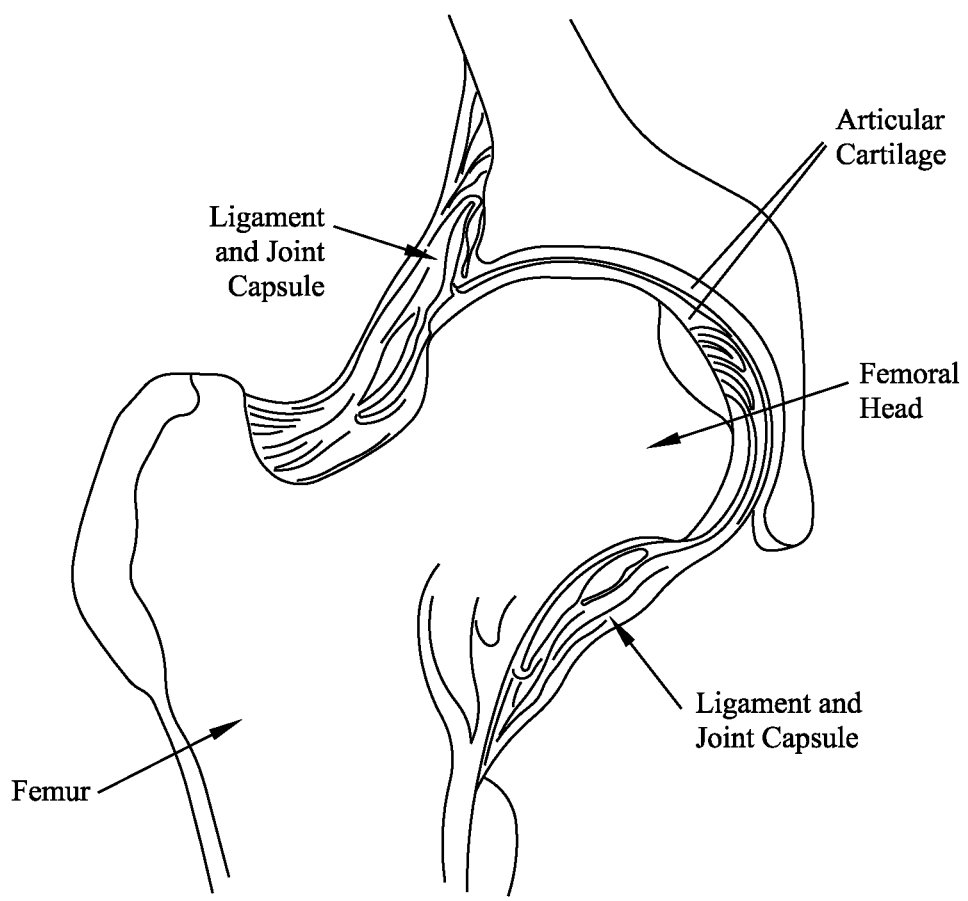
FIGS. 6-12 are schematic views showing the bone and soft tissue structure of the hip joint.
Figure 7:
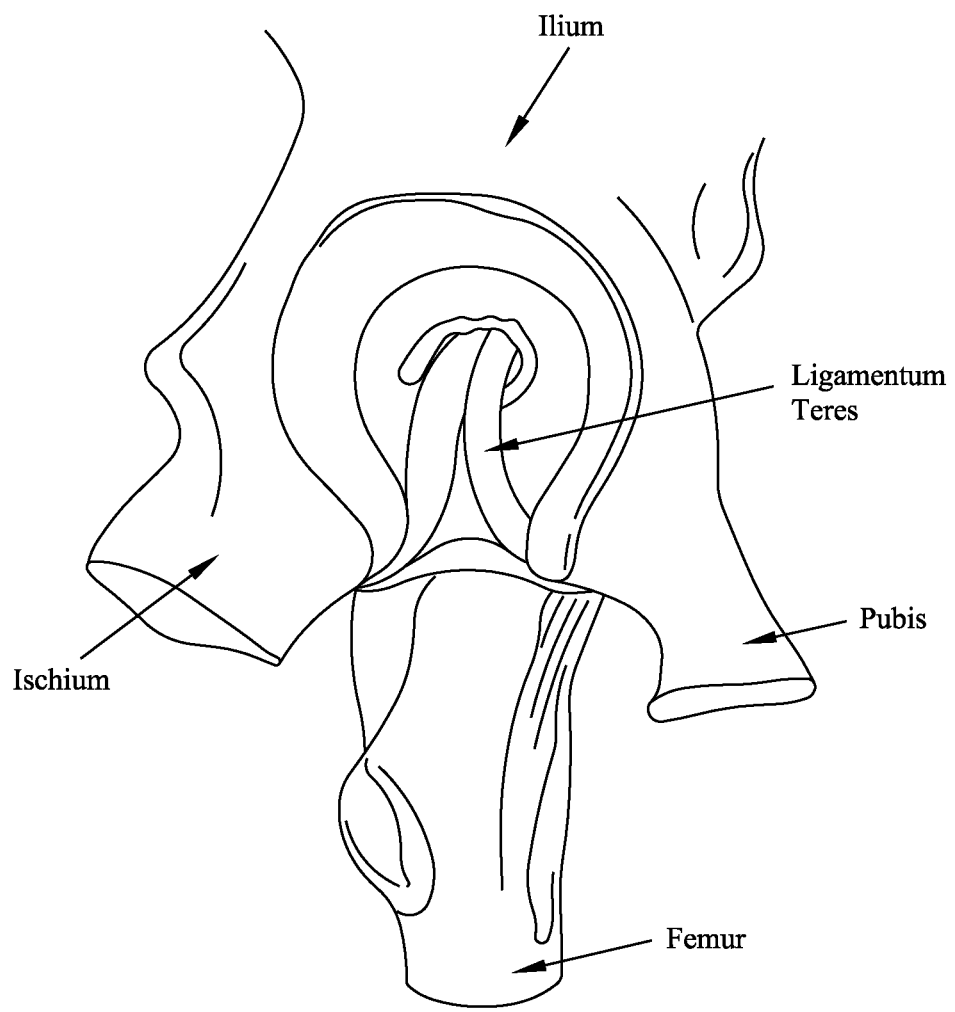
Figure 8:
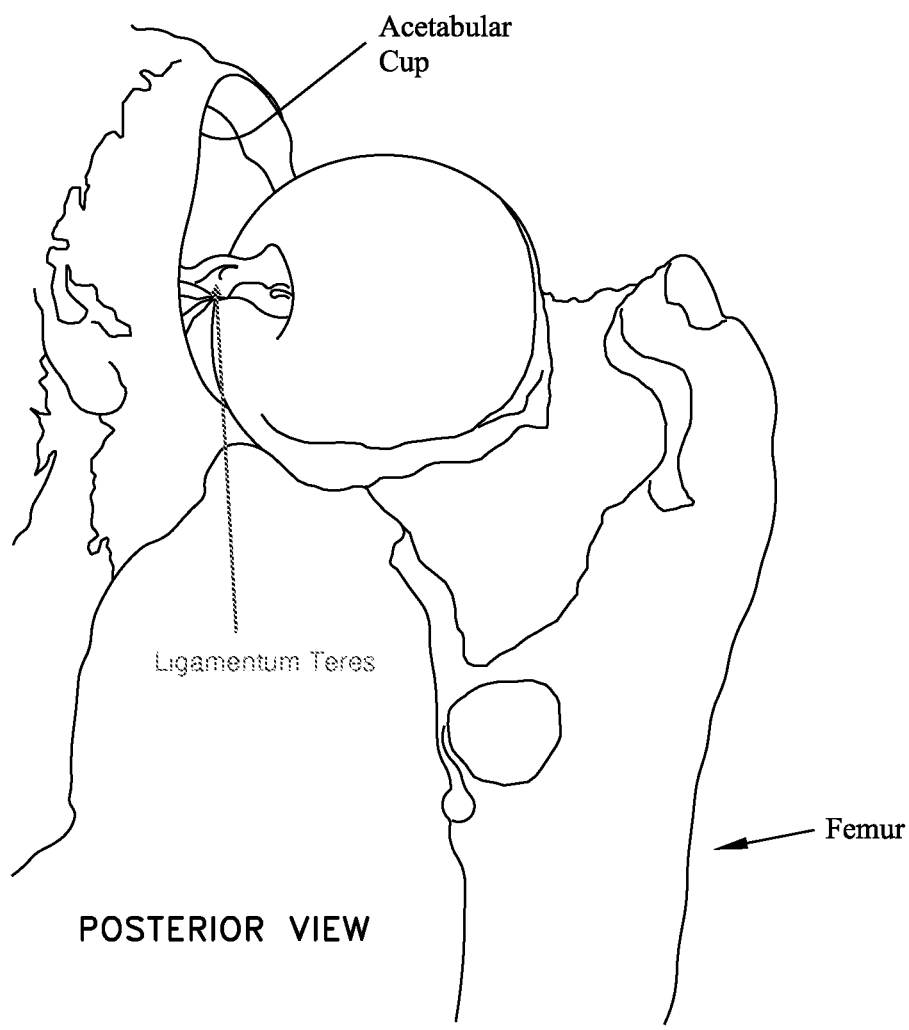
Figure 9:
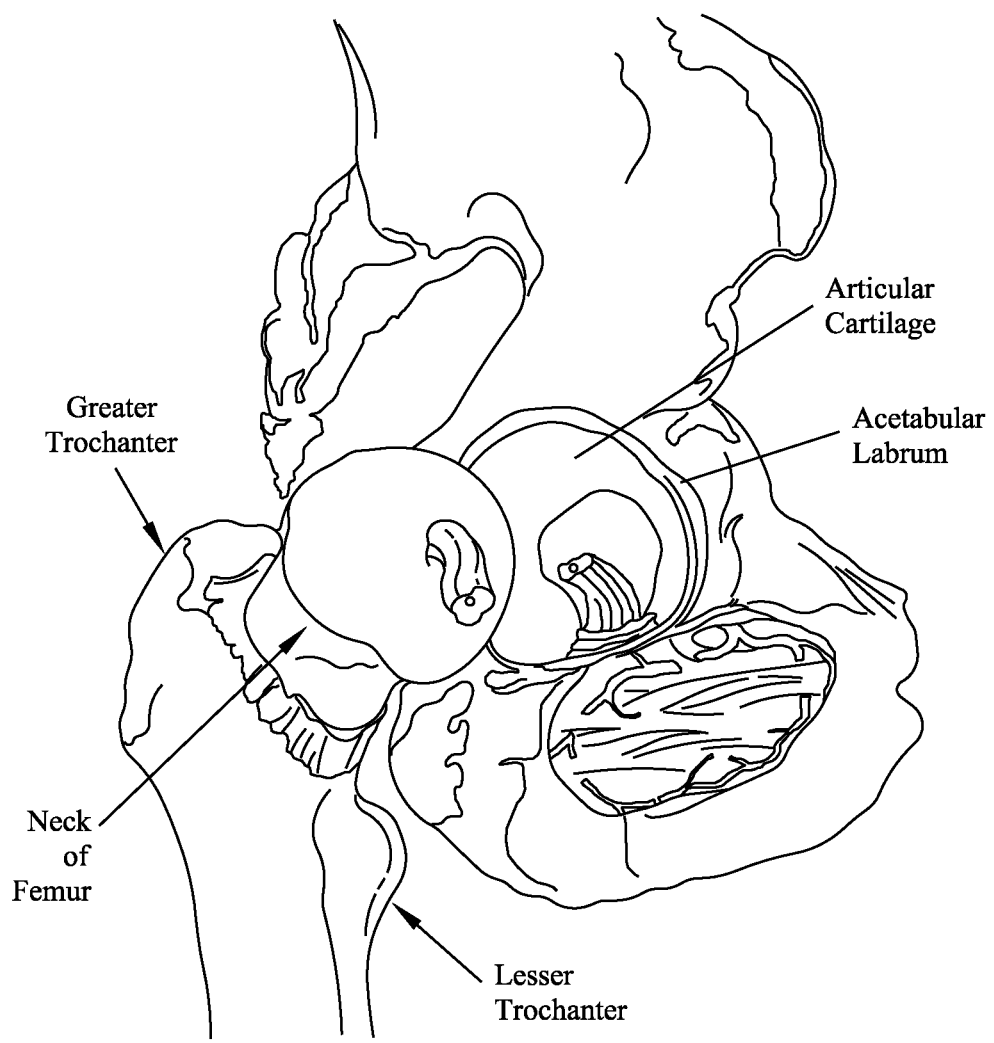
Figure 10:
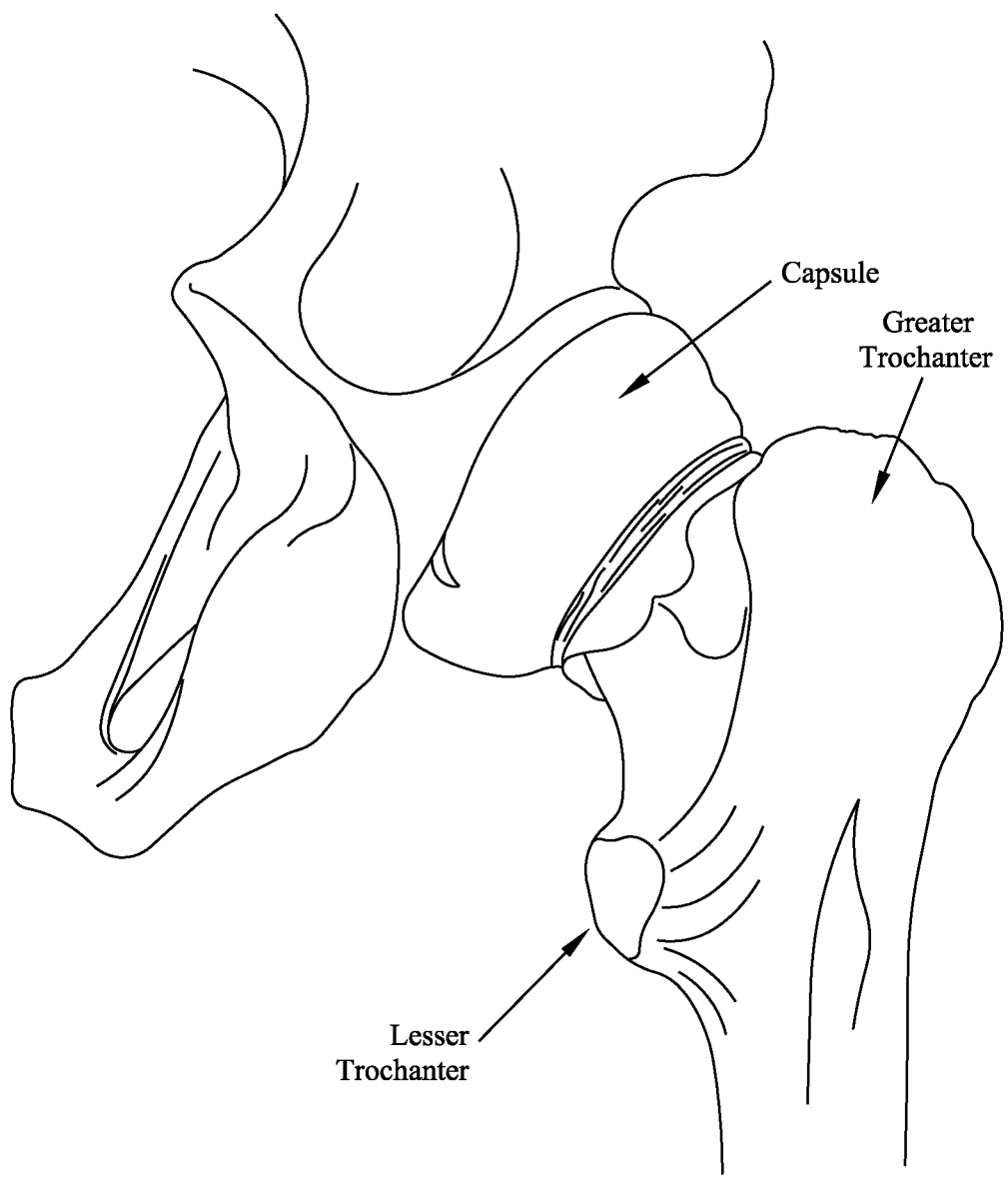
Figure 11:
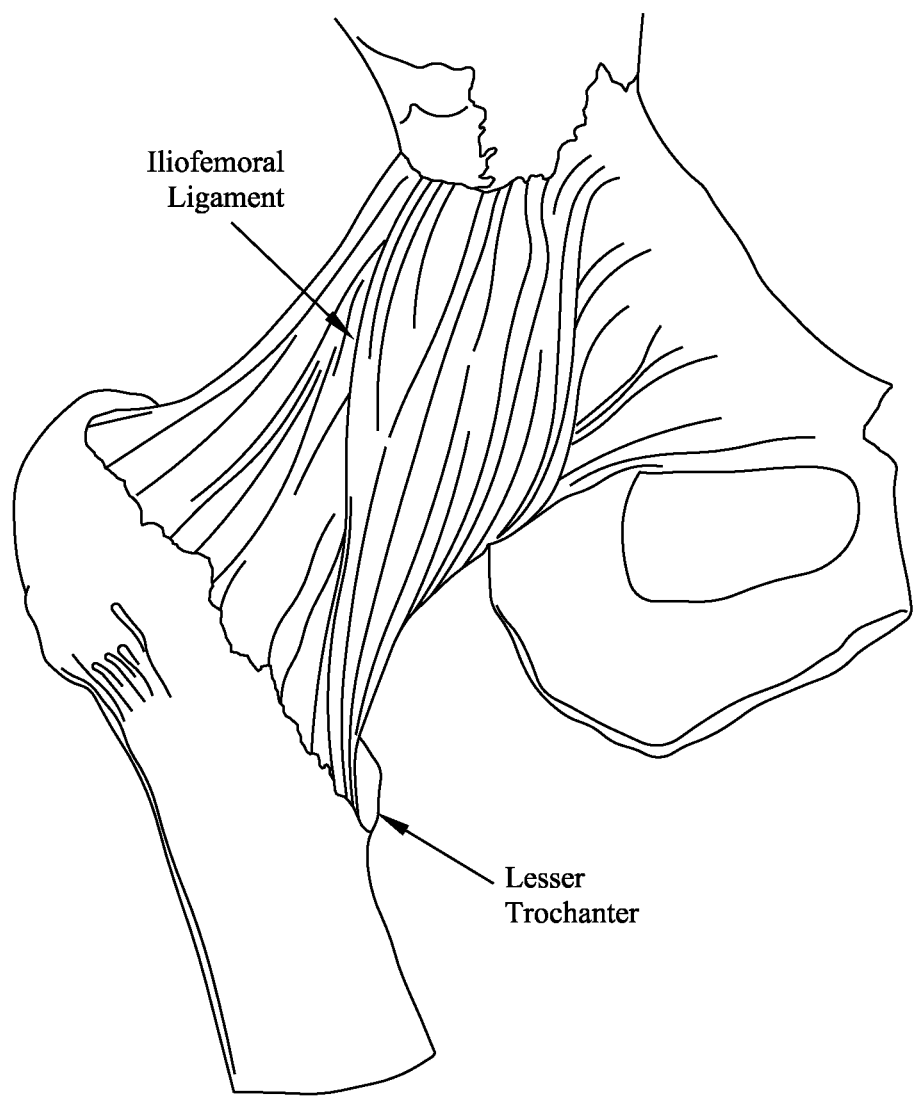
Figure 12:
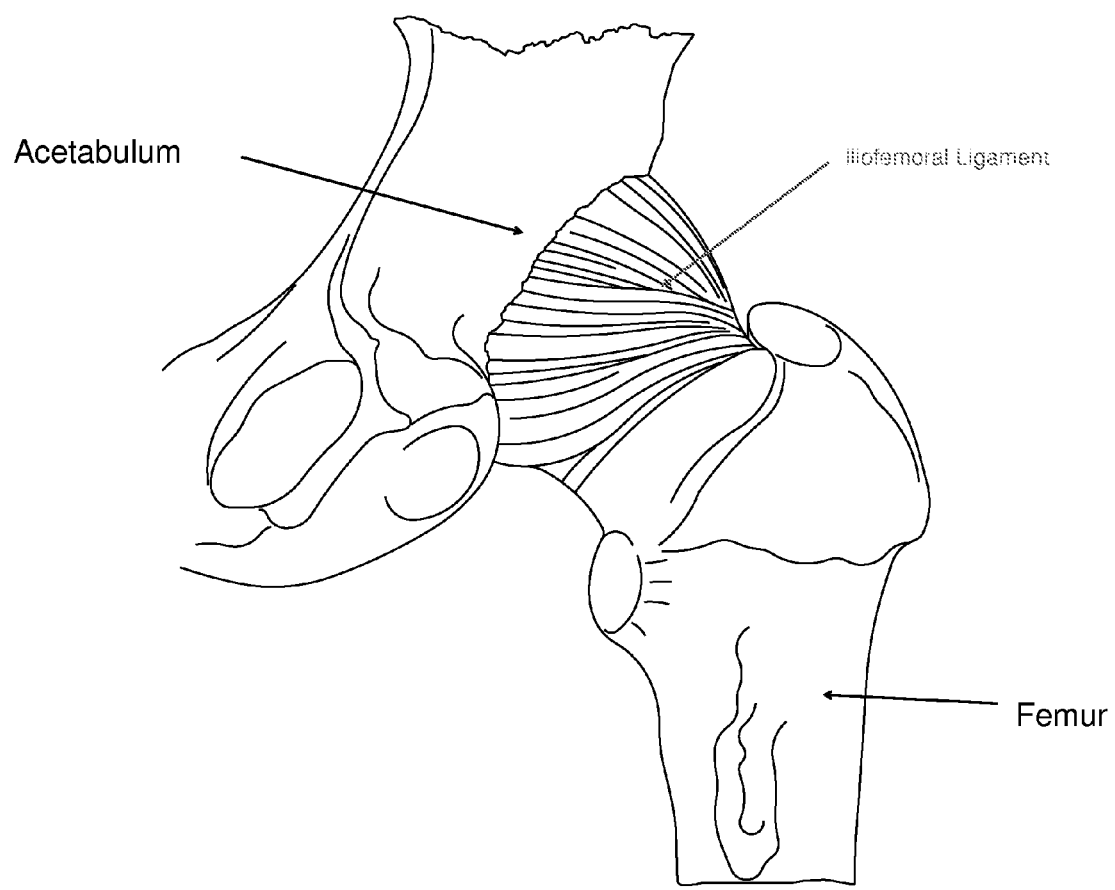
Figure 15:
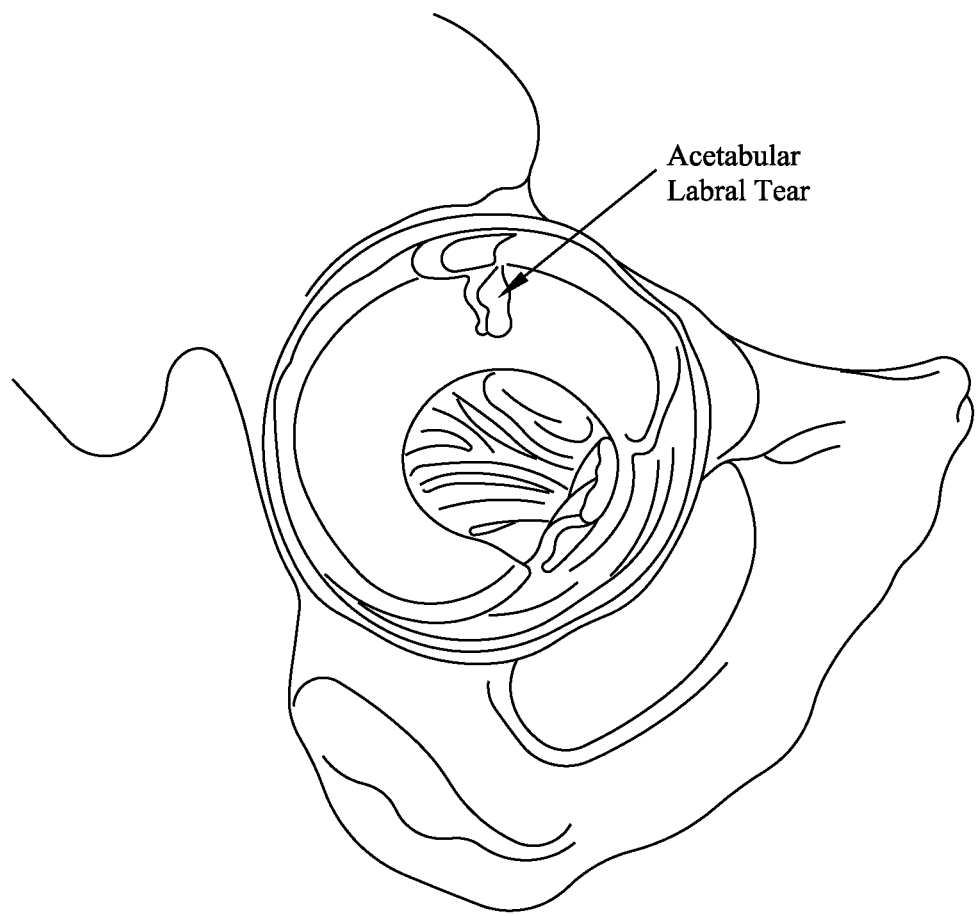
FIG. 15 is a schematic view showing a labral tear.
Figure 16:
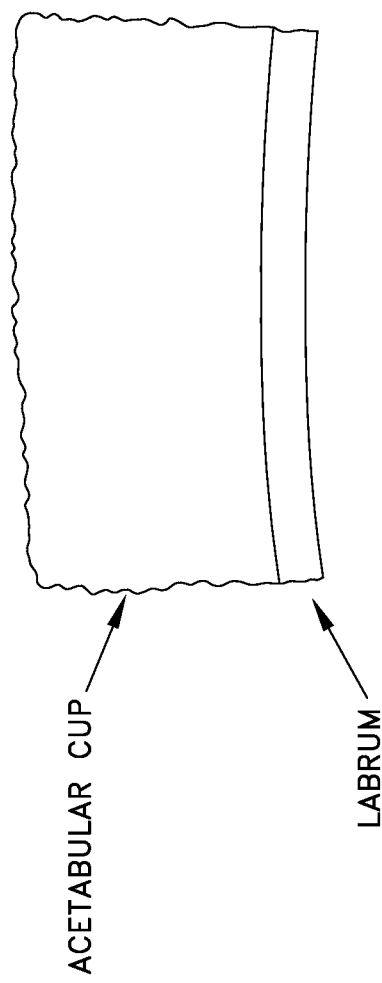
FIG. 16 is a schematic view showing the normal position of the labrum snug against the acetabular cup.
Figure 17:
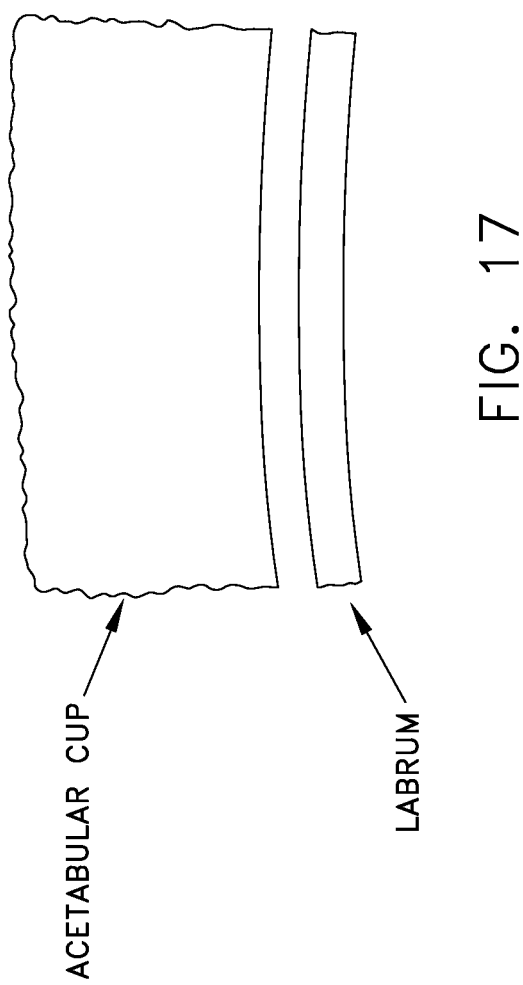
FIG. 17 is a schematic view showing the labrum separated from the acetabular cup.
Figure 18:
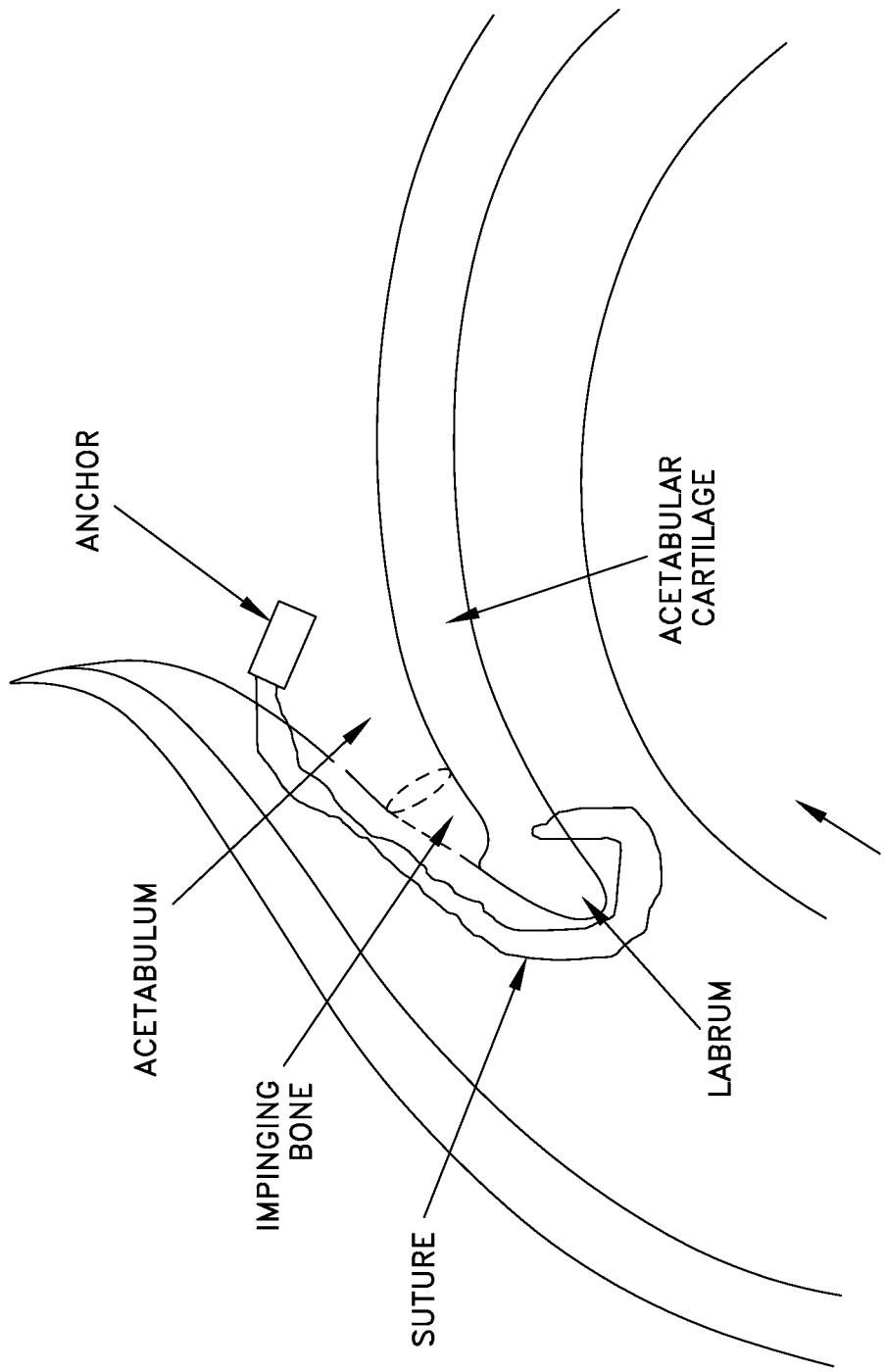
FIG. 18 is a schematic view showing a conventional labrum re-attachment using a bone anchor deployed into the acetabulum shelf.
Figure 19:
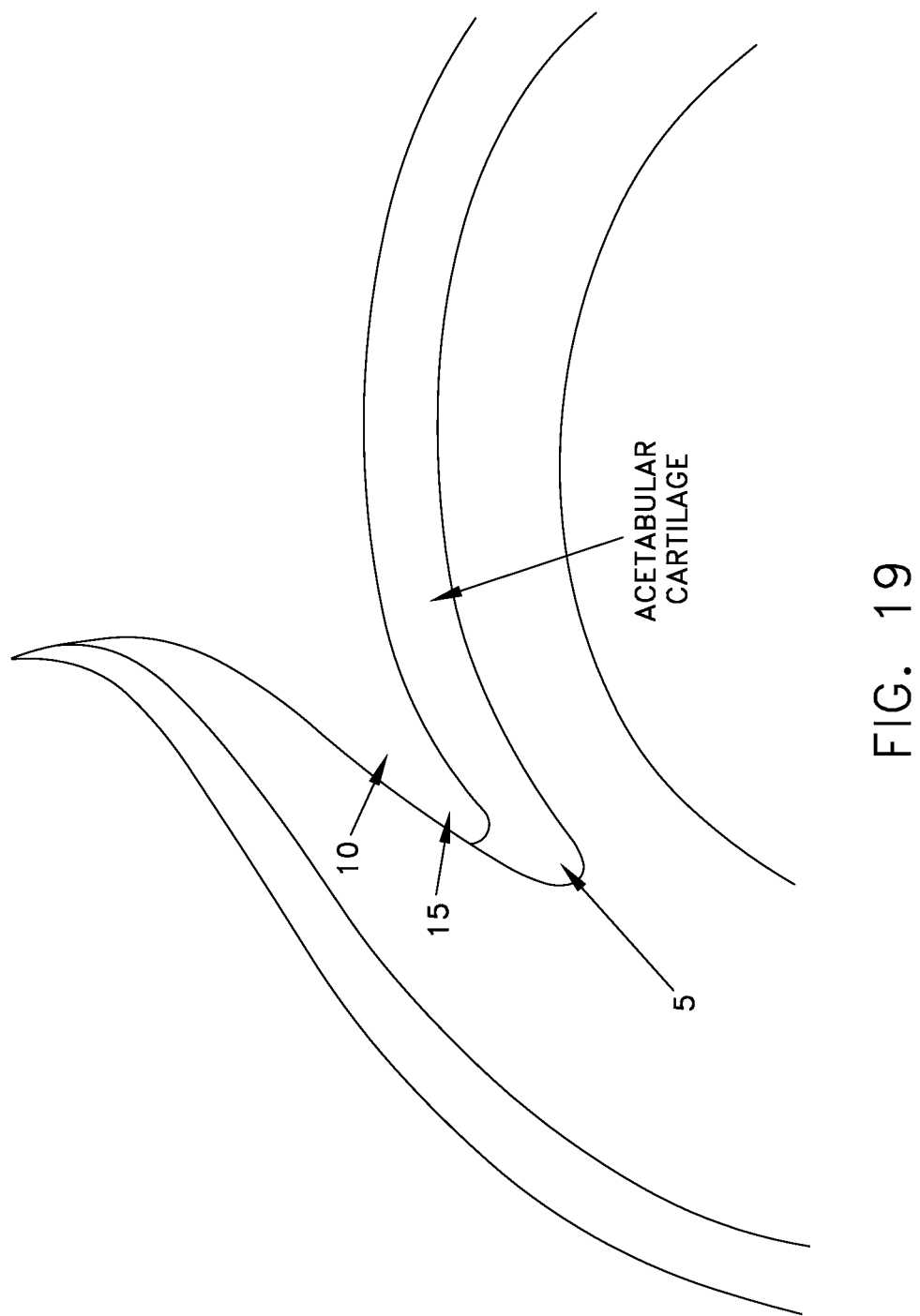
FIGS. 19-30 are schematic views showing a new approach for treating pincer-type FAI, including the provision of a novel method and apparatus for re-attaching the labrum after the acetabulum has been trimmed.
Figure 20:
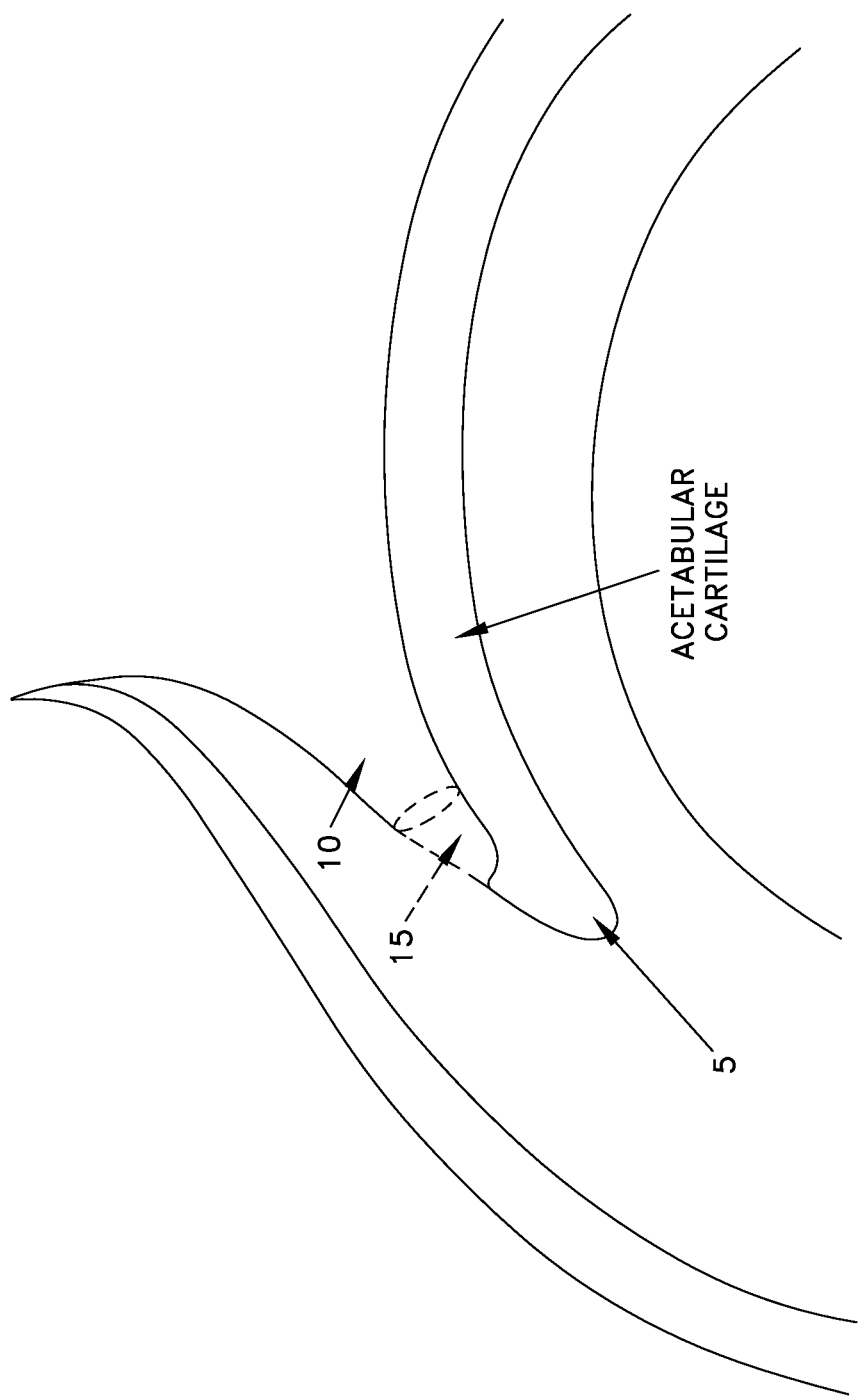
Figure 21:
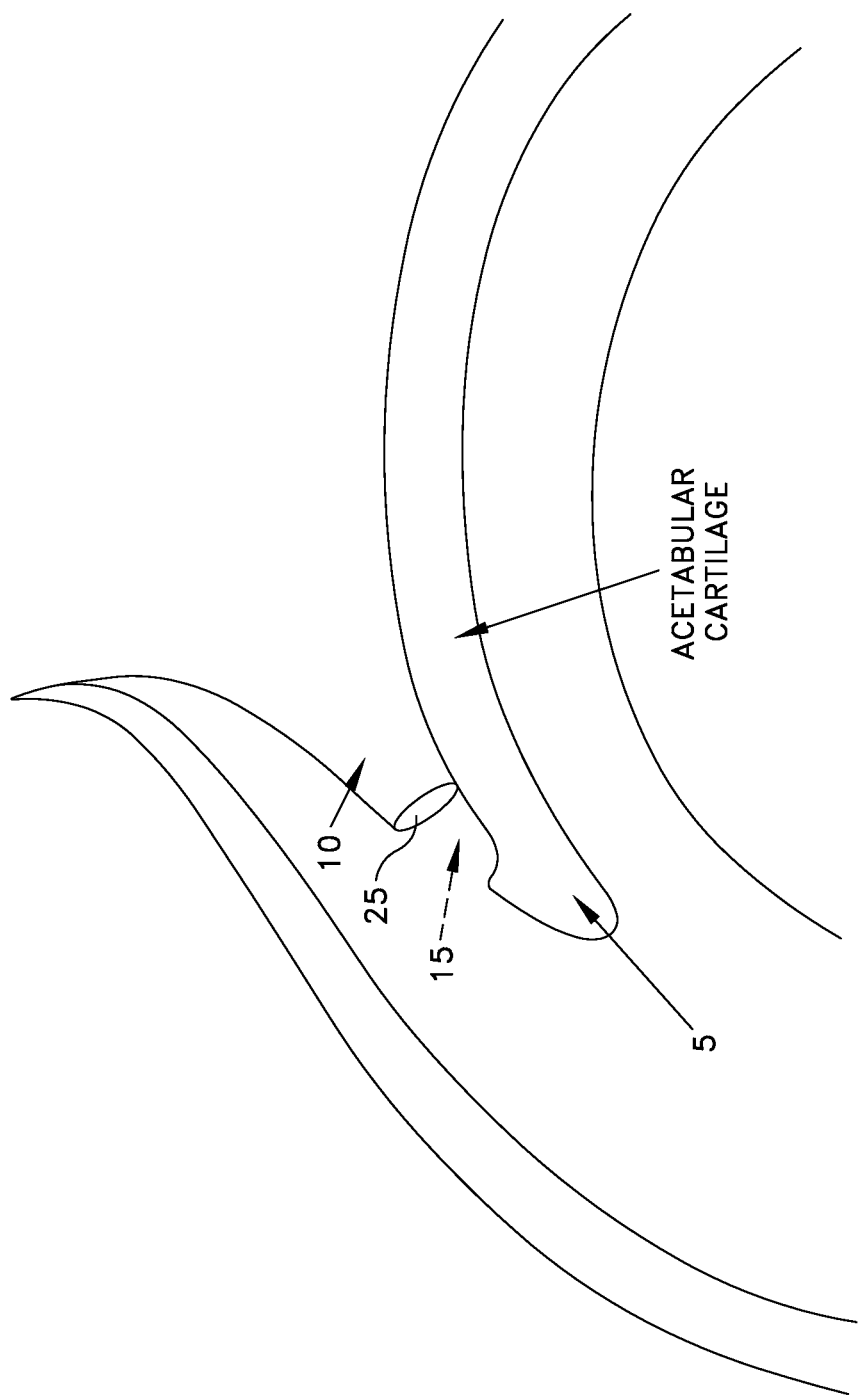

More particularly, and looking now at FIGS. 19-21, when treating pincer-type FAI, it may be desirable to remove the overgrown acetabular portion 15 in order to free the labrum 5 and to alleviate the pincer impingement. Thereafter, it is necessary to secure the freed portion of the labrum to the newly-trimmed rim surface 25 (FIG. 21) of acetabulum 10, in order to facilitate proper healing and restore normal function to the joint.

Figure 22:
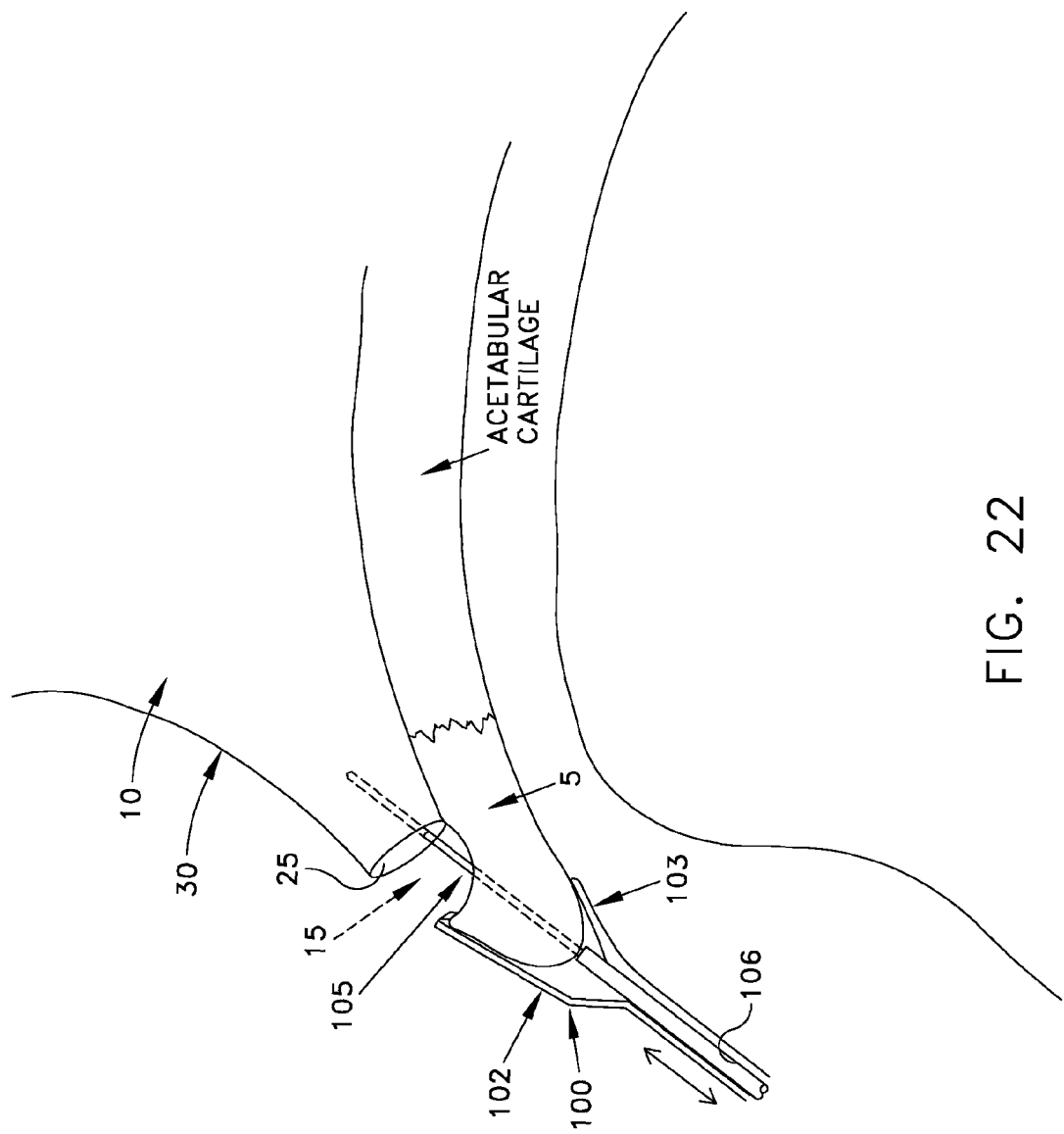

To this end, and looking next at FIG. 22, the freed portion of labrum 5 is grasped by a grasper 100 (e.g., between arms 102, 103) so as to hold the freed portion of labrum 5 stable. Then a guide pin 105 is passed through grasper 100 (e.g., through an interior lumen 106 of grasper 100), through the freed portion of labrum 5 and then into rim surface 25 of acetabulum 10. Guide pin 105 may be provided with a spade tip or other configuration of drilling tip if desired so as to facilitate drilling entry into the acetabular bone.

It should be appreciated that, as seen in FIG. 22, guide pin 105 is introduced into acetabulum 10 through the rim surface 25 created by the pincer debridement. This approach is highly desirable since, as will hereinafter be discussed, it facilitates re-attaching the freed portion of labrum 5 directly to rim surface 25, which provides a superior anatomical fixation. This approach also facilitates rapid tissue ingrowth, since labral re-attachment is effected directly against the highly vascularized and bleeding bone bed 25 created by the trimming process. It should also be appreciated that labral re-attachment directly to rim surface 25 is in marked contrast to prior art labral re-attachment approaches, which typically deploy a suture anchor in the upper surface 30 of the acetabulum (i.e., into the acetabulum shelf). However, as discussed above, anchoring in the acetabulum shelf produces the undesirable eversion effect discussed above, which can interfere with the suction cup function of the labrum. Alternatively, some prior art approaches simply remove otherwise-viable labral tissue in order to access the pincer pathology in order to remove the necessary bone. However, as noted above, this is generally not preferred, since it typically leads to worse long-term outcomes.

Figure 23:
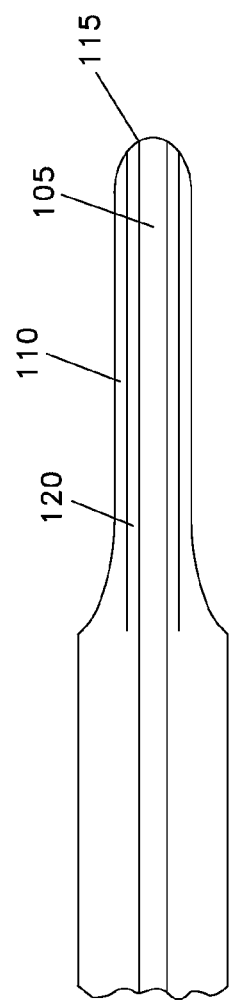
Figure 24:
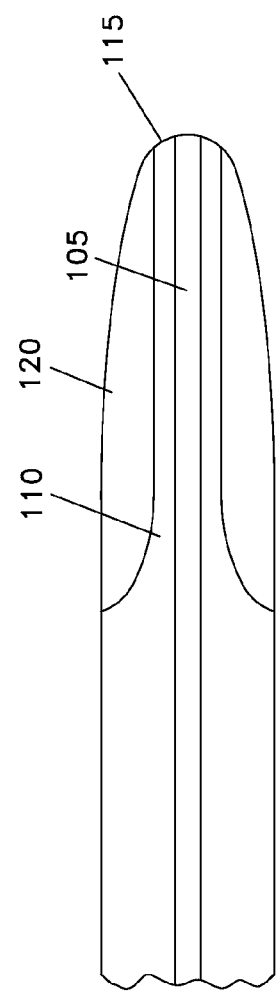
Figure 25:
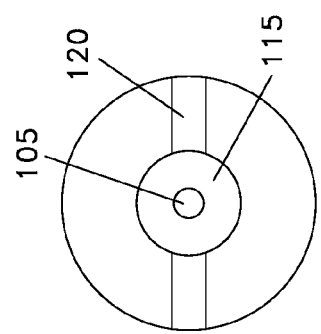
Figure 26:
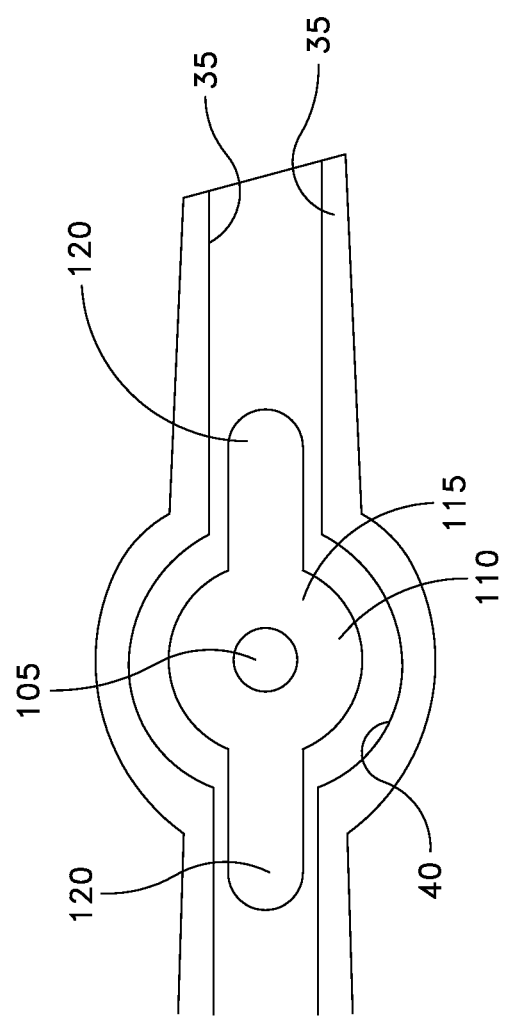

Next, a cannulated blunt obturator 110 (FIGS. 23-25) is passed down guide pin 105 (preferably through a lumen in grasper 100) and through the freed portion of labrum 5 (FIG. 26). More particularly, blunt obturator 110 is characterized by an atraumatic front tip 115 and preferably including a pair of diametrically-opposed wings 120. Atraumatic front tip 115 gently parts the concentric, substantially parallel fibers 35 of labrum 5, and the slightly-trailing wings 120 further separate the concentric, substantially parallel fibers 35, thereby atraumatically providing an opening 40 through the freed portion of labrum 5 without tearing of the labral tissue. Then guide pin 105 is removed, leaving the freed portion of labrum 5 securely gripped by grasper 100 and with obturator 110 extending atraumatically through the freed portion of labrum 5. Then obturator 110 is removed, leaving grasper 100 to maintain the position of labrum 5.

Alternatively, guide pin 105 can remain extending through labrum 5 and into the acetabulum 10 if the trans-labral dart 125 (see below) is cannulated so as to permit an "over-the-wire" delivery of the trans-labral dart. Such an "over-the-wire" approach can be advantageous, since it aids in precise delivery of trans-labral dart 125 through the labrum and into the acetabulum, guided by guide pin 105.

Figure 27:
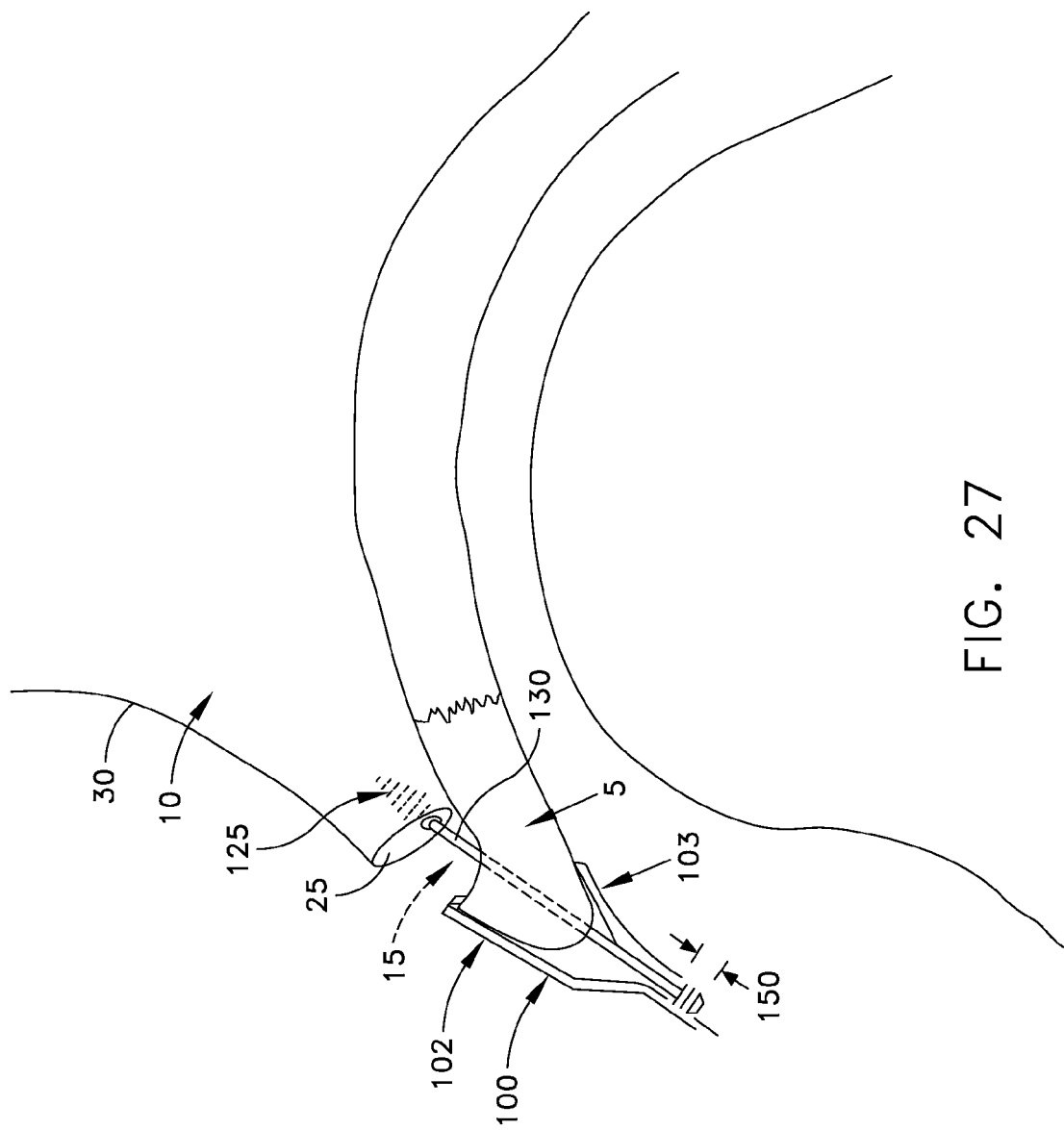

Next, as shown in FIG. 27, a trans-labral dart 125, having a suture (or flexible appendage) 130 attached thereto, is advanced through the freed portion of labrum 5 and into rim surface 25, with suture 130 extending out of rim surface 25 and through the freed portion of the labrum. Trans-labral dart 125 may be threaded, barbed, ribbed or otherwise fashioned, in ways well known in the art, so as to enhance the retention of the trans-labral dart within acetabulum 10. At this point, grasper 100 may be removed from the surgical site.

Figure 28:
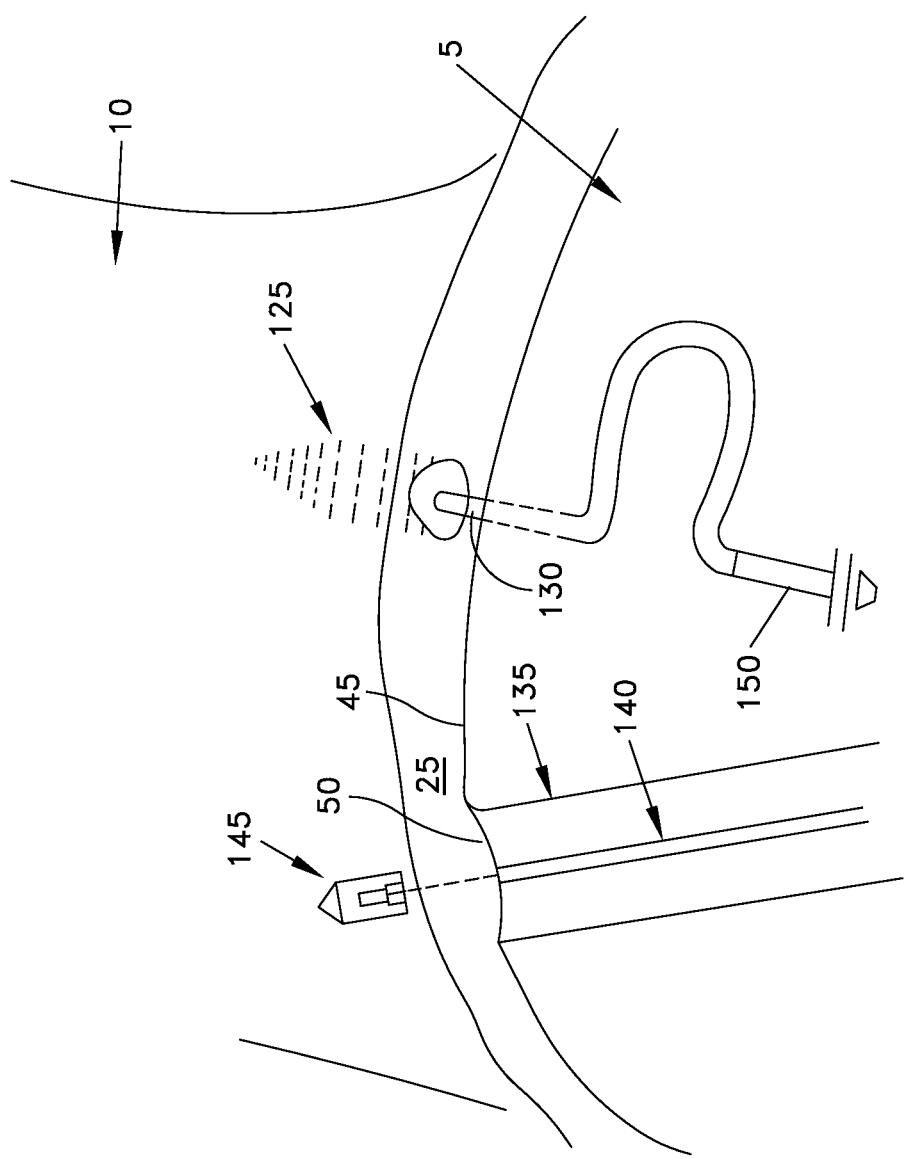

Next, as shown in FIG. 28, a scoop retractor 135 is used to retract the upper edge 45 of the freed portion of labrum 5, e.g. as shown at 50. Then another guide pin 140 is driven into rim surface 25. Guide pin 140 is used to deliver a cannulated anchor 145 (riding down guide pin 145 in an "over-the-wire" delivery) into rim surface 25. Alternatively, anchor 145 need not be advanced in an "over-the-wire" approach, i.e., guide pin 140 can be removed and then anchor 145 advanced, in a "free-handed" manner, into the hole formed by guide pin 140.

Preferably, the entry point of guide pin 140 into the acetabulum is offset from the position of trans-labral dart 125 in both a lateral and vertical sense, for reasons which will hereinafter be discussed in further detail.

Figure 29:
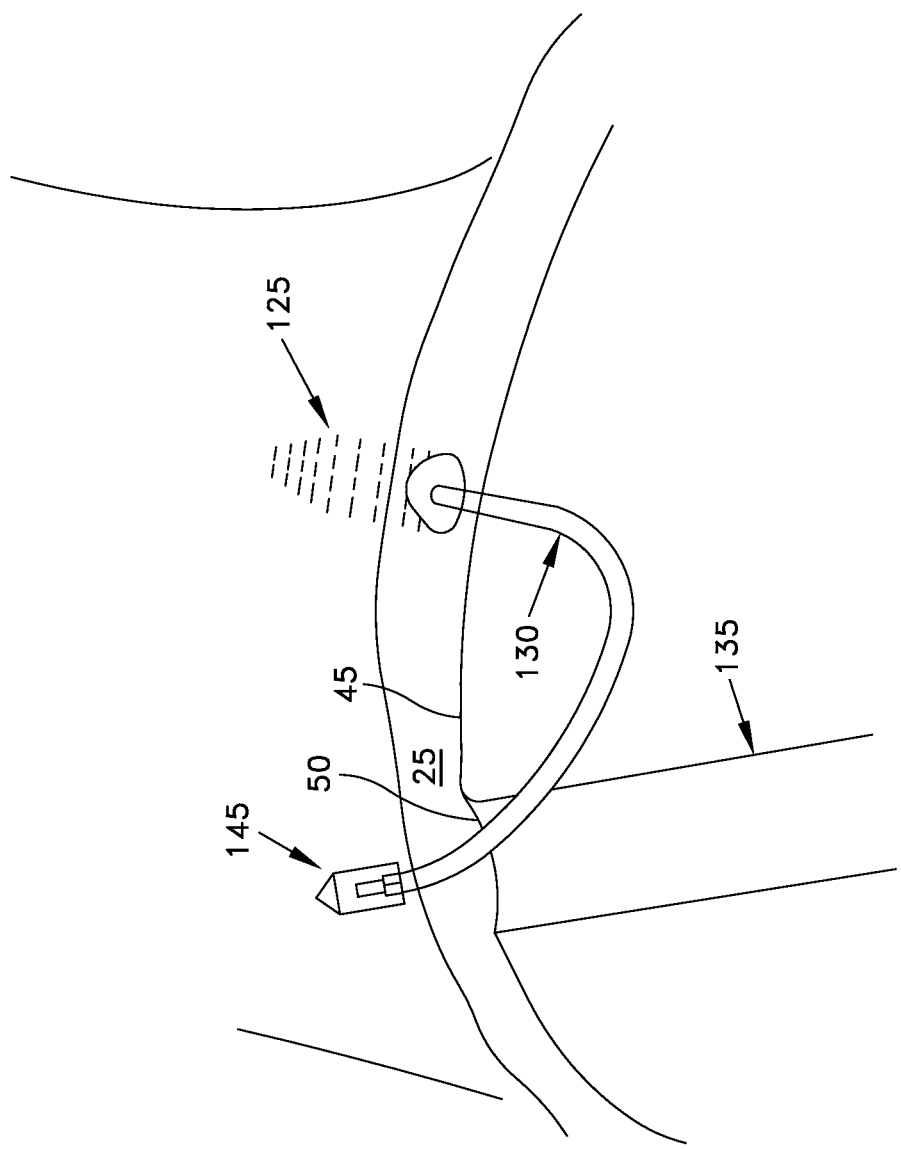

Then, and looking now at FIGS. 28 and 29, a traveler plug 150, secured to the free end of suture or flexible appendage 130 (the other end of which is in turn secured to trans-labral dart 125), is secured in anchor 145. This action results in one end of the suture (or flexible appendage) 130 being set in acetabulum rim surface 25 via trans-labral dart 125, and the other end of the suture (or flexible appendage) 130 being set in acetabulum rim surface 25 via anchor 145 and traveler plug 150, with the intermediate portion of suture 130 extending through the freed portion of labrum 5, whereby to secure the freed portion of labrum 5 to acetabulum rim surface 25.

As noted above, attaching labrum 5 to acetabulum 10 via anchoring devices (e.g., trans-labral dart 125 and anchor 145) set directly into rim surface 25, provides anatomic refixation of the labrum to the acetabulum. This is a marked improvement over prior art labral refixation approaches, which are effected via anchors set into the upper shelf of the acetabulum and which suffer from the aforementioned eversion problems. In addition, by re-attaching the labrum directly to the debrided rim surface 25, tissue ingrowth is enhanced, inasmuch as rim surface 25 provides a highly vascularized and bleeding bone bed due to the debridement procedure.

Figure 30:
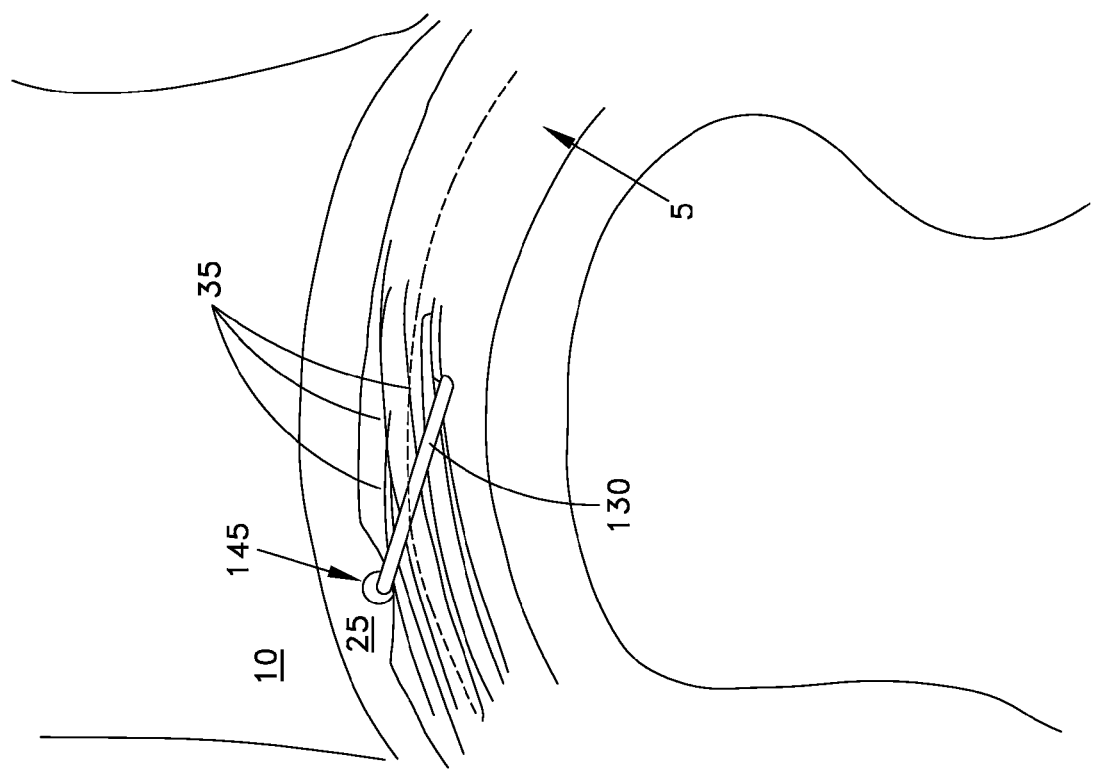

Also, and looking now at FIG. 30, by both laterally and vertically offsetting the entry point of guide pin 140 into the acetabulum from the entry point of trans-labral dart 125 into the acetabulum, suture 130 can be made to pass across a number of parallel fibers 35, whereby to securely attach labrum 5 to acetabulum 10. Specifically, this approach helps prevent a passed suture from pulling through the labrum. The surgeon can control the tightness of the suture 130 by regulating how far the travel plug 150 travels within the female recess of the anchor 145. Additionally, the labrum refixation construct of the present invention renders no man-made materials within the hip joint surfaces as contrasted with current techniques and devices. By placing the suture 130 on the capsular side (i.e., outside of the joint), erosion of the hip joint cartilage surfaces can be avoided.

Double-Armed Tissue Dart

Figure 31:
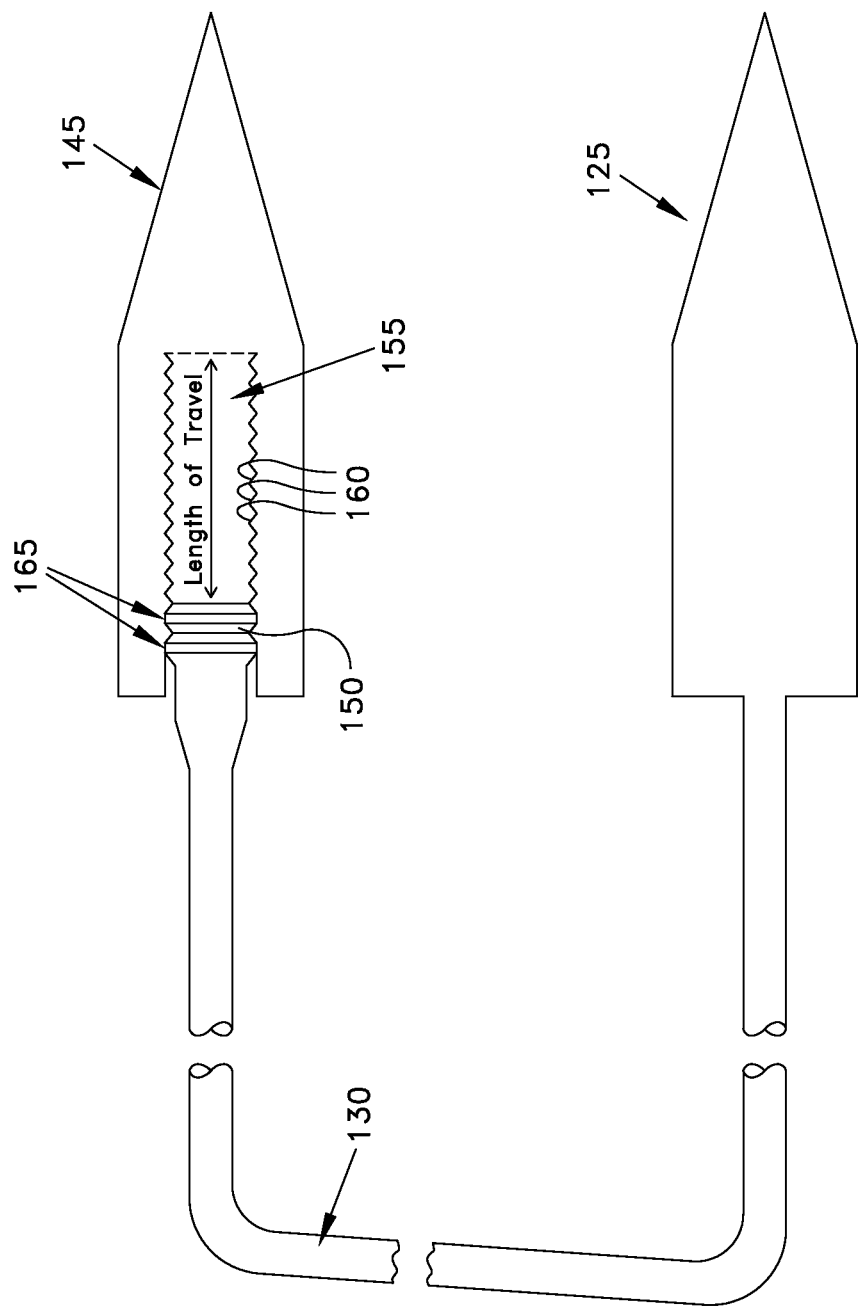
FIG. 31 is a schematic view showing novel apparatus for use in securing the labrum to the acetabulum.

In the foregoing description, the labrum is re-attached to the acetabulum using (i) a trans-labral dart 125 having a suture (or flexible appendage) 130 extending therefrom, with a traveler plug 150 formed on the free end of suture (or flexible appendage) 130, and (ii) an anchor 145 which receives traveler plug 150. See FIG. 31. To this end, bone anchor 145 preferably includes a distally extending recess 155 including a plurality of ratchet teeth 160, and traveler plug 150 preferably comprises one or more annular ribs 165 for ratchet-like engagement with ratchet teeth 160. Thus, traveler plug 150 can be reliably secured to bone anchor 145 with a ratchet action, with suture 130 being appropriately tensioned or loosened according to the extent of travel of traveler plug 150 within recess 155. This approach is highly advantageous, since it obviates the need to tie suture knots, thus providing knotless fixation, and provides a means to cinch the suture between tissue dart 125 and bone anchor 145.

Furthermore, by using a dual-channeled slotted cannula, tissue dart 125 and bone anchor 145 can be simultaneously passed through the labrum and into their bone anchorages. Furthermore, by slotting the dual-channeled cannula, suture 130 (which is attached to tissue dart 125 on one end and bone anchor 145 on the other end) can be released from the dual-channeled cannula.

Figure 32:
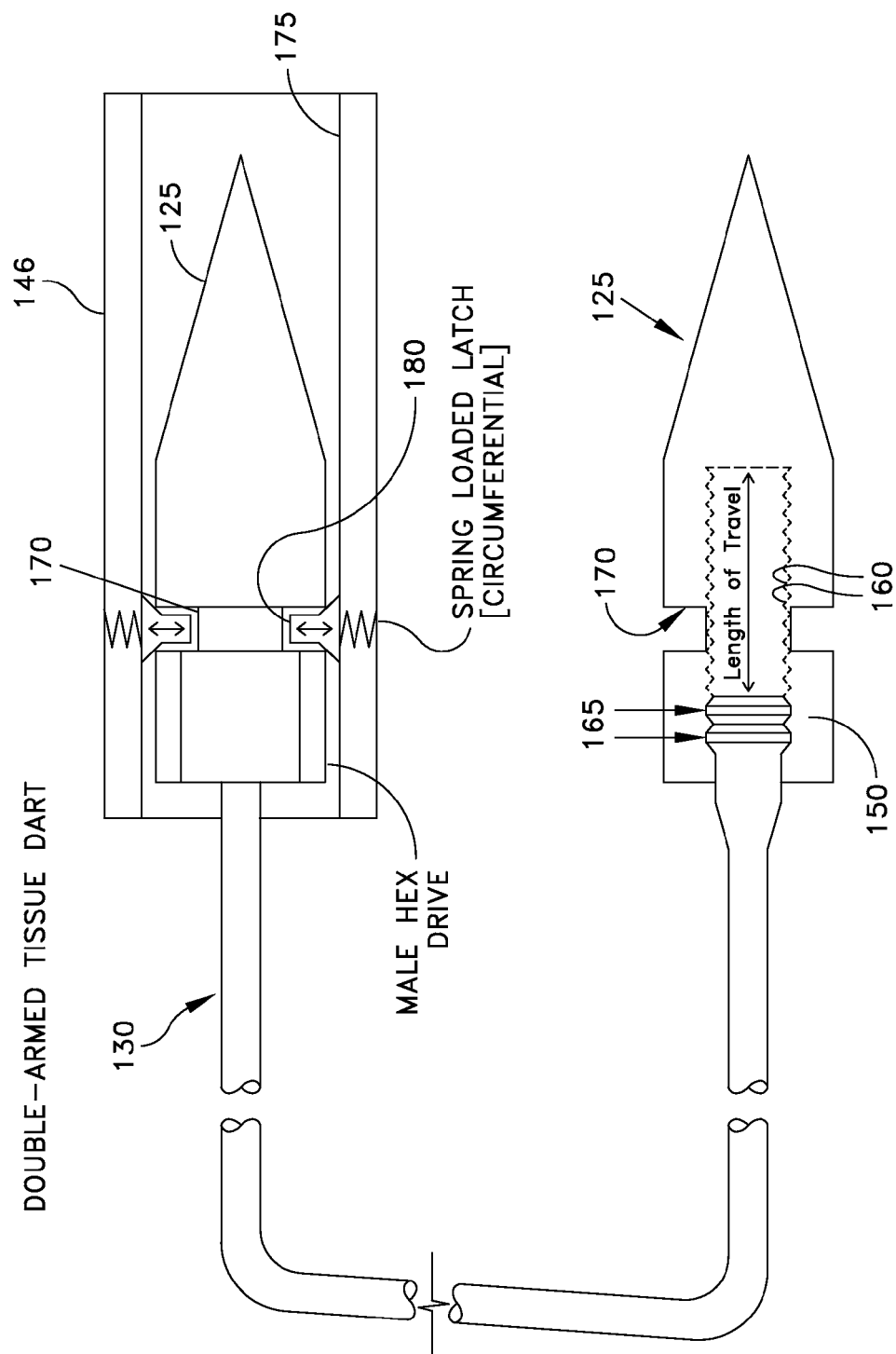
FIG. 32 is a schematic view showing other novel apparatus for use in securing the labrum to the acetabulum.

It is also possible to embody this concept in alternative constructions. Thus, for example, and looking now at FIG. 32, there is shown a construction wherein suture 130 has a tissue dart 125 disposed at each end thereof, with each end of suture 130 being variably secured to tissue dart 125 via a traveler plug 150 and the aforementioned ratchet mechanism 160, 165. Furthermore, one or both tissue darts 125 can be secured within a bone anchor 146 which is itself deployed into bone, e.g., by providing each tissue dart with a circumferential groove 170 and each bone anchor with a longitudinally extending recess 175 and one or more radially-extendible, spring-biased fingers 180. With this construction, a tissue dart 125 may be driven directly into bone, or it may be seated within a bone anchor 146 after the bone anchor has been set in bone. Furthermore, the longitudinal position of the traveler plug 150 may be adjusted within the body of tissue dart 125, so as to tension the suture and thereby "cinch" the labrum against the acetabular rim in a controlled fashion.

Fixation with Single Labral Dart

Figure 33:
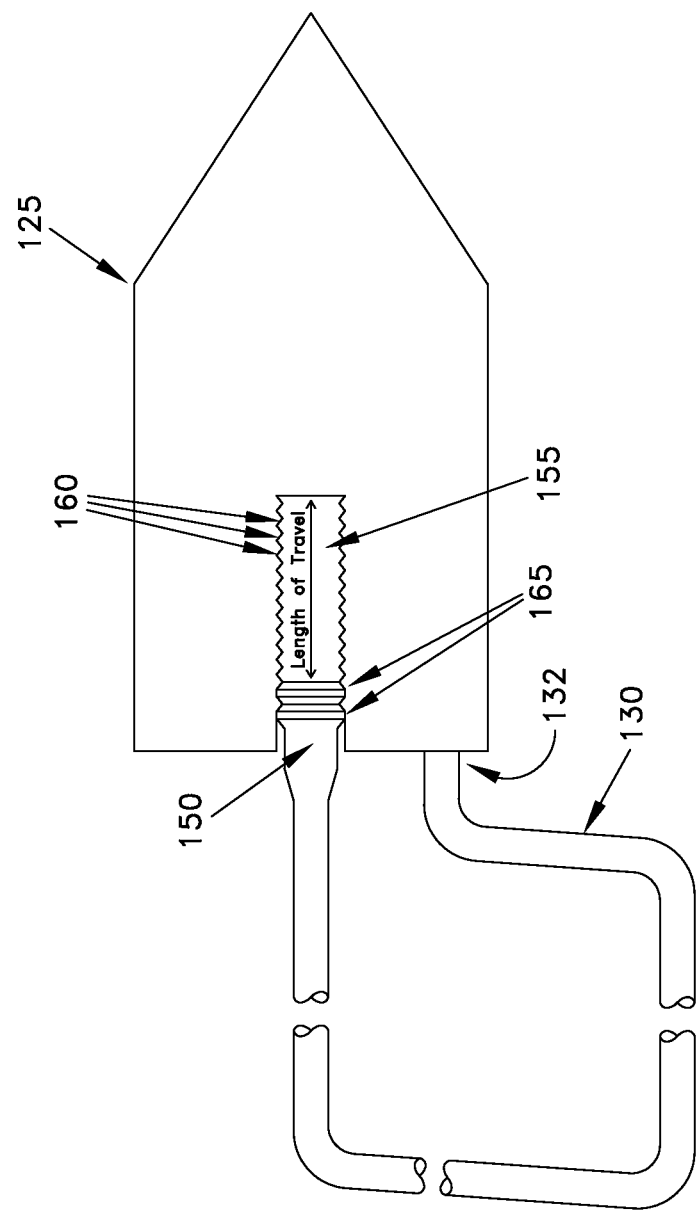
FIG. 33 is a schematic view showing additional novel apparatus for use in securing the labrum to the acetabulum.

It is also possible to effect labral fixation with a single labral dart. More particularly, and looking now at FIG. 33 there is shown a labral dart 125 having a suture 130 fixedly secured thereto at 132. The free end of suture 130 has a traveling plug 150 formed thereon. Traveling plug 150 is received in the longitudinal recess 155 of labral dart 130, with annular ribs 165 of traveling plug 150 engaging ratchet teeth 160 of trans-labral dart 125, whereby to form a ratchet mechanism.

Figure 34:
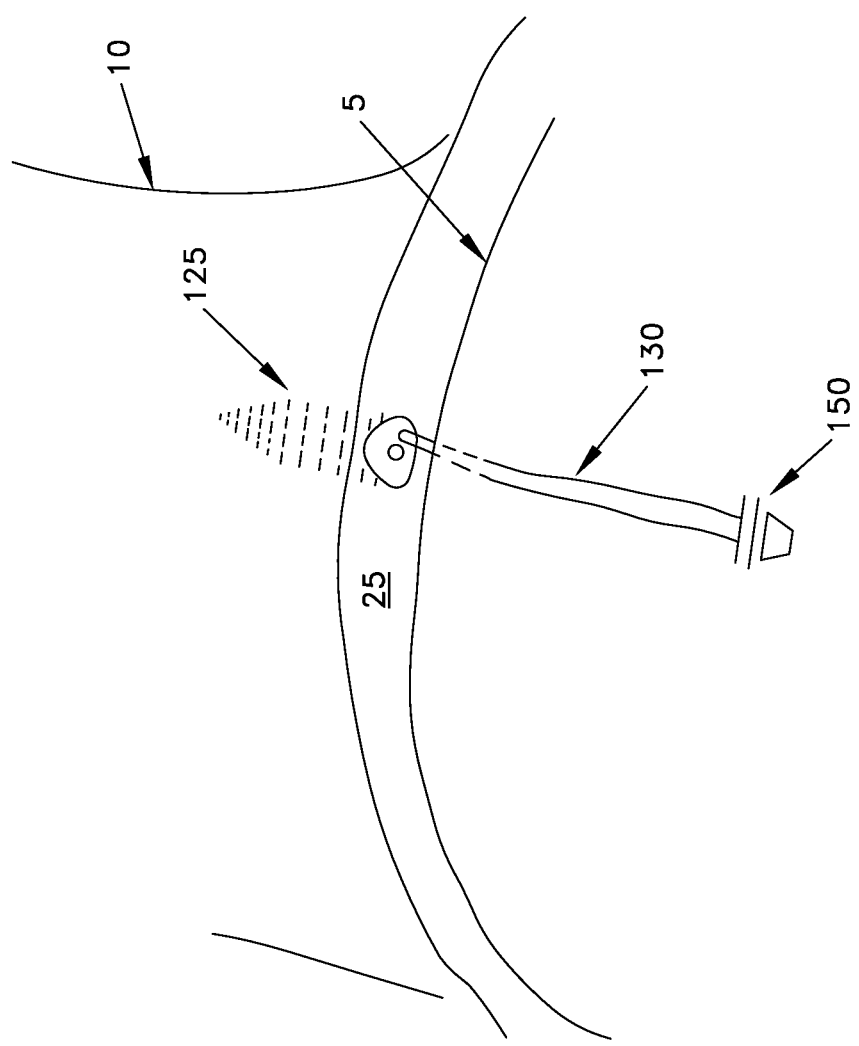
FIGS. 34 and 35 are schematic views showing the apparatus of FIG. 33 being used to secure the labrum to the acetabulum.
Figure 35:
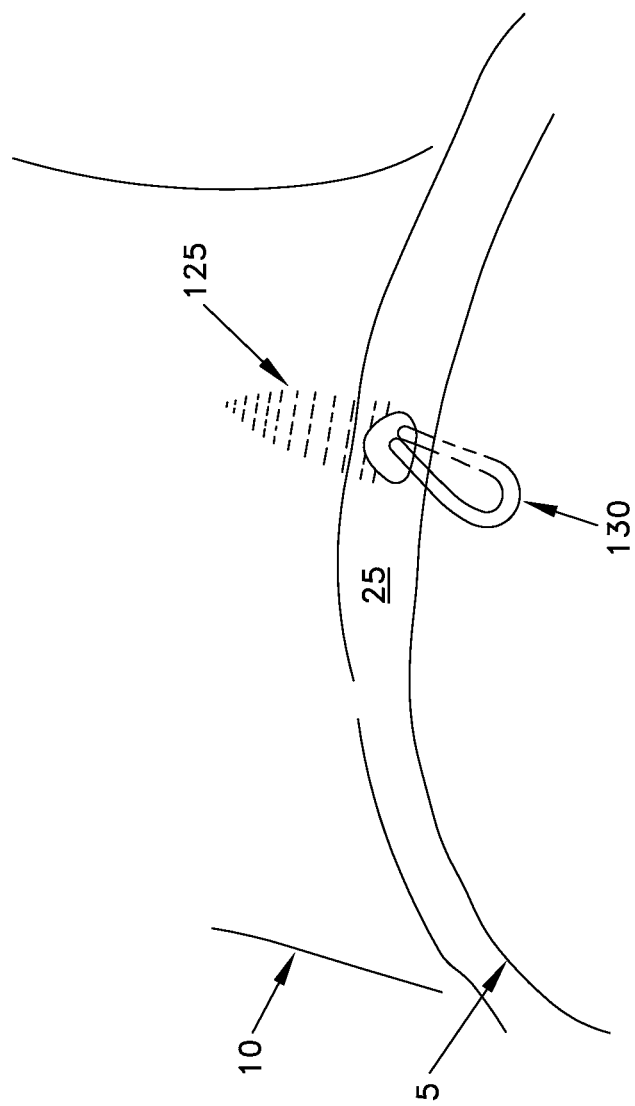

In use, trans-labral dart 125 is passed through labrum 5 and into acetabulum 10, with suture 130 extending from trans-labral dart 125 through labrum 5 (FIG. 34), and then traveling plug 150 is installed in recess 155 so as to secure the free end of the suture loop to trans-labral dart 125. In this respect it will be appreciated that the ratchet mechanism effected between annular ribs 165 of traveling plug 150 and ratchet teeth 160 of trans-labral dart 125 will permit suture 130 to be snugged to the extent required to secure labrum 5 in the desired position.

Trans-Labral Dart with Collet

Figure 36:
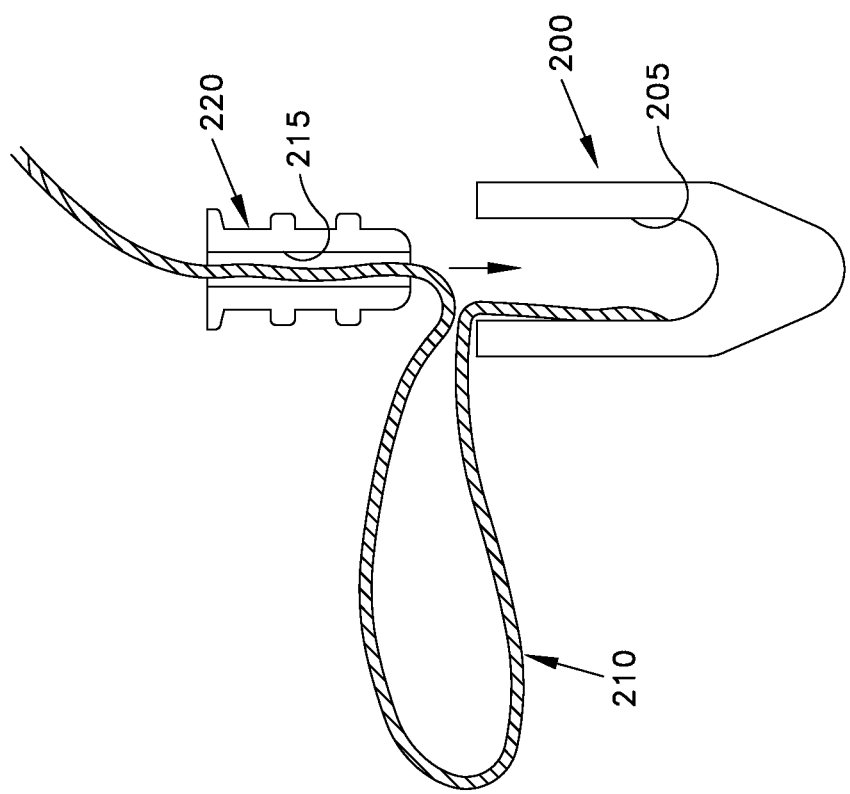
FIG. 36 is a schematic view showing additional novel apparatus for use in securing the labrum to the acetabulum.

Looking next at FIG. 36, there is shown a trans-labral dart 200 having a distally-extending recess 205 formed therein. One end of a length of suture 210 is secured within distally-extending recess 205. The other end of suture 210 passes through a longitudinally-extending bore 215 formed in a collet 220. Longitudinally extending bore 215 is sized so that suture 210 can normally slide easily through the bore; however, collet 220 is formed out of a compressible material, and is sized, so that when collet 220 is forced into longitudinally-extending bore 205 of trans-labral dart 200, the longitudinally-extending bore 215 of collet 220 closes down so as to grip the suture and immobilize it.

Figure 37:
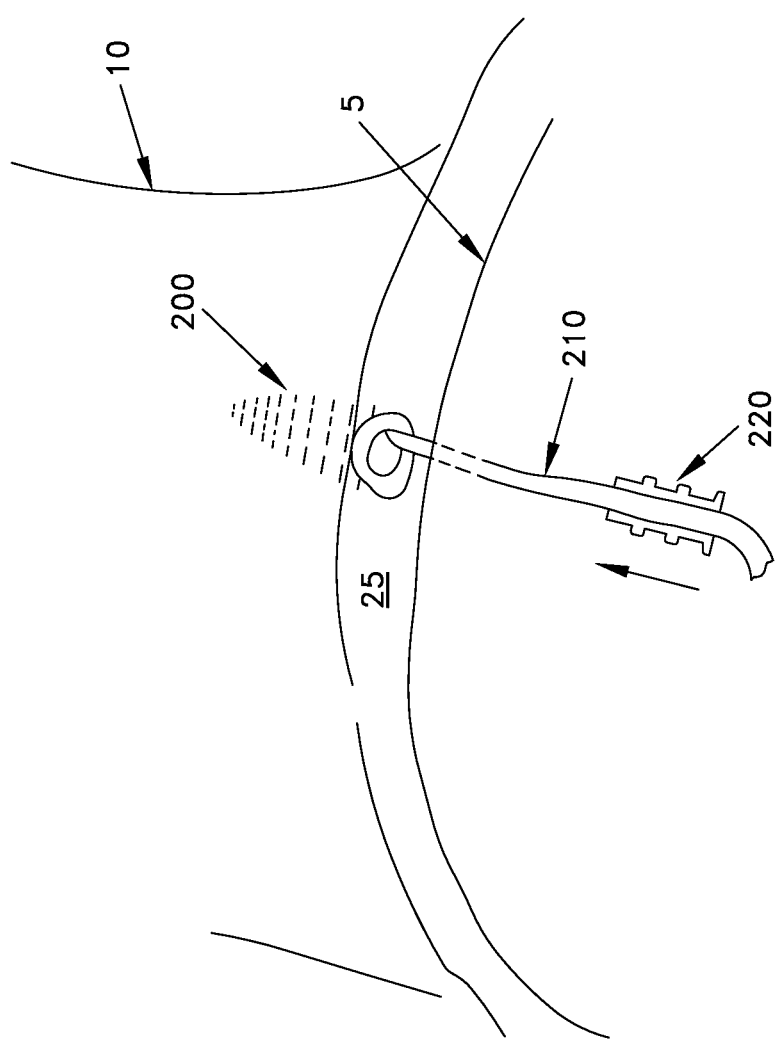
FIGS. 37 and 38 are schematic views showing the apparatus of FIG. 36 being used to secure the labrum to the acetabulum.
Figure 38:
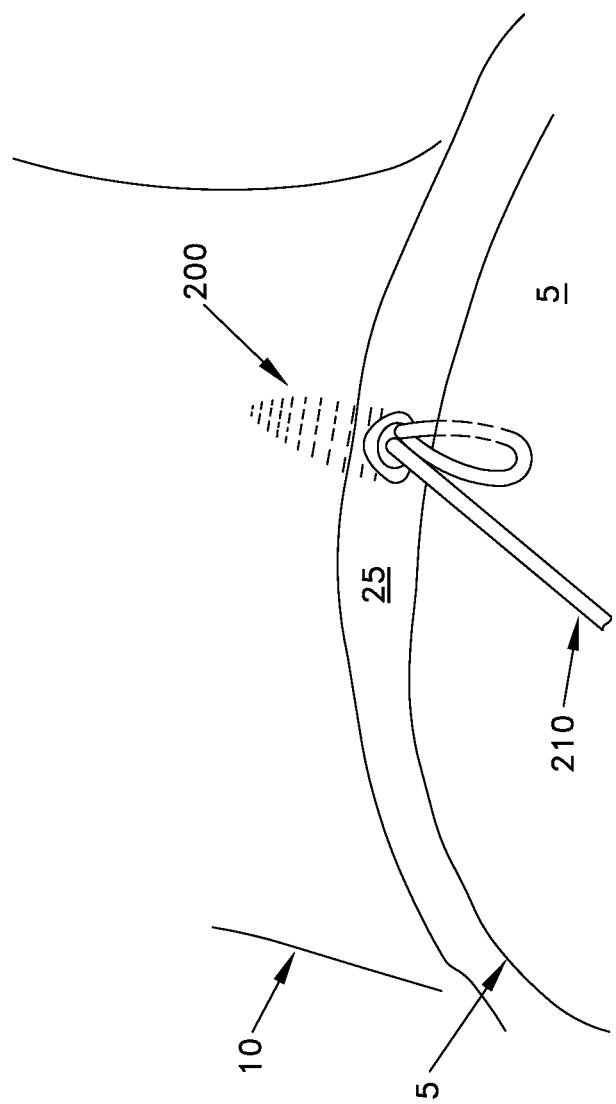

In use, and looking now at FIG. 37, trans-labral dart 200 is passed through labrum 5 and into acetabulum 10, with suture 210 extending from trans-labral dart 200 through labrum 5, and then collet 220 is forced into longitudinally-extending bore 205 of trans-labral dart 200, thereby compressing the collet and securing the suture to the collet 220, and hence trans-labral dart 200, and hence acetabulum 10. See FIG. 38.

Alternatively, dart 200 can be advanced directly into the acetabulum without passing through the labrum, the free end of the suture can next be passed through the labrum, and then collet 220 forced into longitudinally-extending bore 205 of dart 200, thereby compressing the collet and securing the suture to collet 220, and hence dart 200, and hence acetabulum 10.

It should be appreciated that the free end of the suture may be trimmed away in ways well known in the art after collet 220 has been set in trans-labral dart 200.

Stitching the Labrum to the Acetabulum with a Multi-Anchor Suture Strand

It is also possible to stitch the labrum to the acetabulum with a multi-anchor suture strand.

Figure 39:
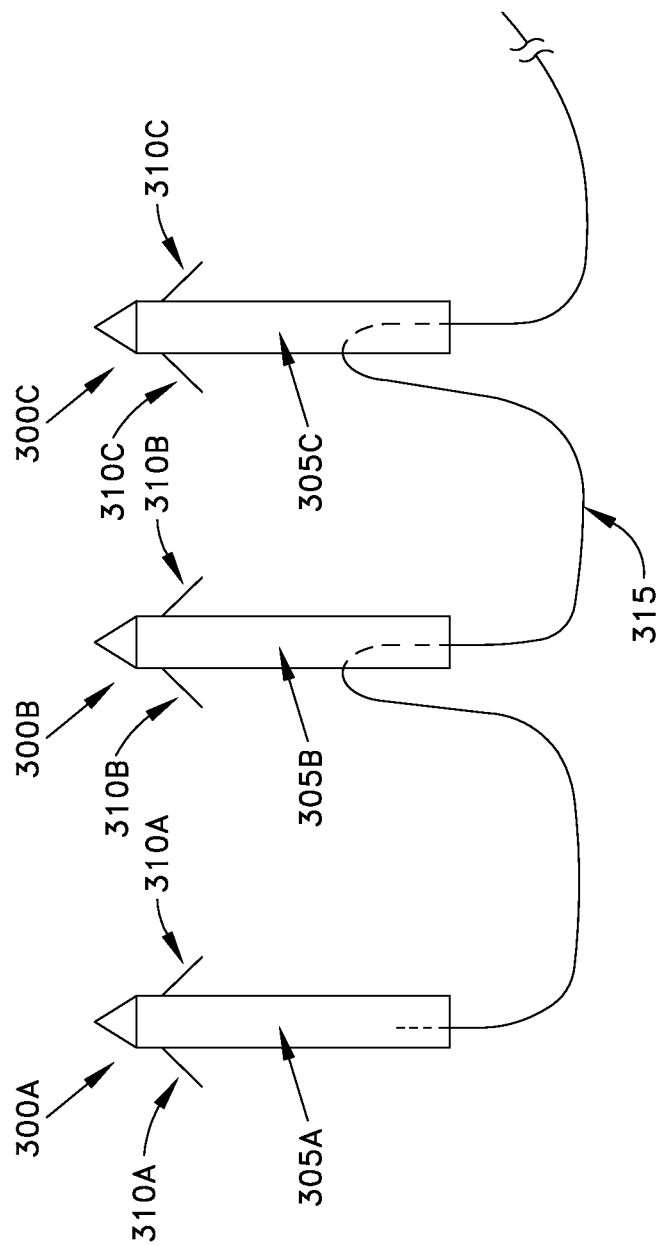
FIG. 39 is a schematic view showing additional novel apparatus for use in securing the labrum to the acetabulum.

More particularly, and looking now at FIG. 39, there is shown a plurality of suture anchors 300A, 300B, 300C, etc. Each of the suture anchors comprises a body 305A, 305B, 305C, etc. and means for holding that body in the acetabulum, e.g., barbs 310A, 310B, 310C, etc. Suture anchors 300A, 300B, 300C, etc. are connected by a suture strand 315. Suture strand 315 may be fixedly secured to each of the suture anchors 300A, 300B, 300C, etc., or suture strand 315 may be slidably secured to one or more of the suture anchors, e.g., suture anchor 305B, 305C, etc.

Figure 40:
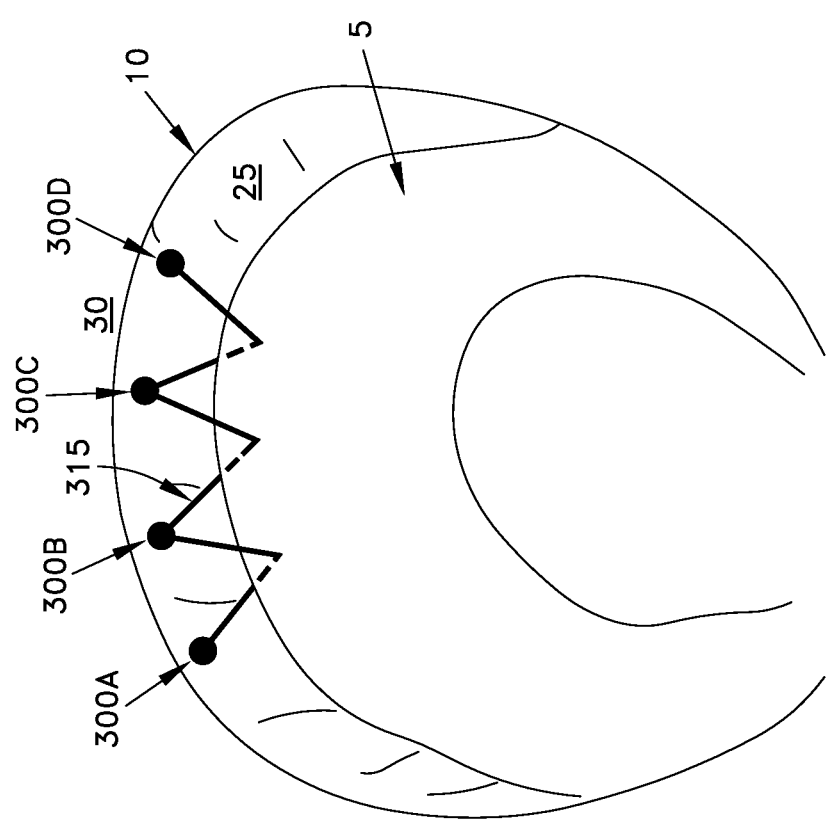
FIG. 40 is a schematic view showing the apparatus of FIG. 39 being used to secure the labrum to the acetabulum in a first manner.

In use, and looking now at FIG. 40, suture anchor 300A is set in rim surface 25, the adjacent portion of suture strand 315 is passed through a portion of labrum 5, suture anchor 300B is set in a spaced location elsewhere in rim surface 25, the adjacent portion of suture strand 315 is passed through another portion of labrum 5, and so on, in the manner of FIG. 40, until labrum 5 has been stitched to rim surface 25.

Figure 41:
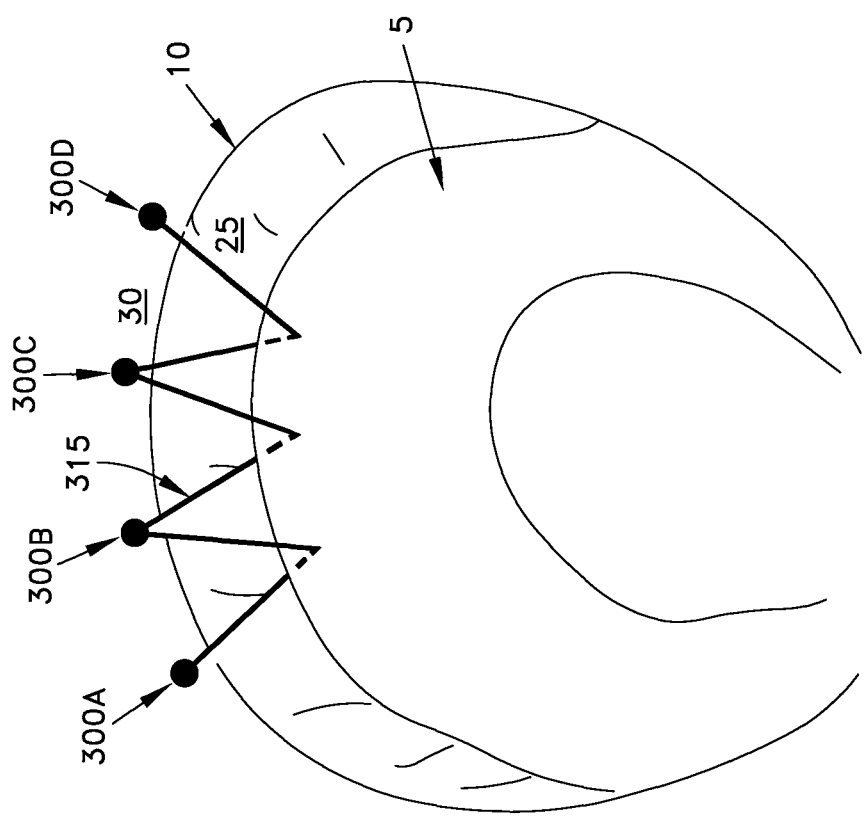
FIG. 41 is a schematic view showing the apparatus of FIG. 39 being used to secure the labrum to the acetabulum in a second manner.

In another use of the apparatus of FIG. 39, and looking now at FIG. 41, suture anchors 300A, 300B, 300C, etc. may be set in the acetabulum shelf 30, above rim surface 25, in order to stitch labrum 5 to acetabulum 10.

Use of the Novel Method and Apparatus for Other Joints, Etc.

It should be appreciated that the novel method and apparatus of the present invention may be used for procedures other than a pincer-type FAI reconstruction, and/or for attaching suture (or flexible appendage) to other tissues and the like in order to attach such tissue to the acetabulum, and/or may be used for attaching suture (or flexible appendage) to other tissues and the like in order to attach them to other bodily structures. By way of example but not limitation, the novel method and apparatus of the present invention may be used to attach suture (or flexible appendage) to soft tissue and prostheses in the shoulder joint, etc.

Modifications of the Preferred Embodiments

It should be understood that many additional changes in the details, materials, steps and arrangements of parts, which have been herein described and illustrated in order to explain the nature of the present invention, may be made by those skilled in the art while still remaining within the principles and scope of the invention.

What is claimed is:

1. A method for treating pincer-type femoroacetabular impingement (FAI), comprising:
    removing an overgrown portion of the acetabulum so as to provide newly-trimmed acetabular rim surface and a detached portion of the labrum;
    passing a guide through the detached portion of the labrum and into the newly-trimmed acetabular rim surface;
    passing a securement mechanism along the guide and into the newly-trimmed acetabular rim surface so as to secure the detached portion of the labrum to the newly-trimmed acetabular rim surface; and
    removing the guide from the newly-trimmed acetabular rim surface and the detached portion of the labrum.

2. A method according to claim 1 wherein a suture connects the detached portion of the labrum to the at least one securement mechanism.

3. A method according to claim 2 wherein at least two securement mechanisms are used to secure the detached portion of the labrum to the newly-trimmed acetabular rim surface, wherein the suture is attached to the at least two securement mechanisms, and further wherein the suture extends through the labrum.

4. A method according to claim 1 wherein the securement mechanism comprises a trans-labral dart.

5. A method according to claim 1 wherein the securement mechanism comprises a suture anchor.

6. A method according to claim 1 wherein the guide is a guide pin.

7. A method according to claim 1 wherein a hole is drilled in the newly-trimmed acetabular rim surface.

8. A method according to claim 7 wherein the hole is drilled with a drill bit.

9. A method according to claim 7 wherein the drill bit is passed through the detached portion of the labrum using the guide.

10. A method according to claim 8 wherein the detached portion of the labrum is grasped by a grasper.

11. A method according to claim 10 wherein a hole is drilled in the newly-trimmed acetabular rim surface while the detached portion of the labrum is being grasped by the grasper.

12. A method according to claim 10 wherein the guide is passed through the grasper and into the newly-trimmed acetabular rim surface.

13. A method according to claim 12 wherein a hole is drilled in the newly-trimmed acetabular rim surface with a drill bit using the guide.

14. A method according to claim 1 further comprising providing a length of suture having a first end and a second end; and
    wherein the securement mechanism comprises:
        a body having a recess and a distal tip configured for passing through the detached portion of the labrum and into the newly-trimmed acetabular rim surface, the first end of the suture being fixedly secured to the body of the securement mechanism; and
        a compressible collet having a bore therethrough and being selectively receivable within the recess of the body of the securement mechanism, wherein the collet is configured to slidably receive the suture therethrough when the collet is outside the recess of the body of the securement mechanism, and further wherein the collet is configured to compress the bore and grip the suture when the collet is within the recess of the body of the securement mechanism.

15. A method according to claim 14 wherein securing the detached portion of the labrum to the newly-trimmed acetabular rim surface comprises:
    passing the body of the securement mechanism through the detached portion of the labrum and into the newly-trimmed acetabular rim surface; and
    passing the collet over the second end of the suture and down the length of the suture and into the recess so as to create a cinched loop of suture securing the detached portion of the labrum to the securement mechanism and hence to the newly-trimmed acetabular rim surface.

* * * * *